United States Patent
Ehninger et al.

(10) Patent No.: US 10,085,791 B2
(45) Date of Patent: *Oct. 2, 2018

(54) UNIVERSAL SELF-LIMITING ELECTROSURGICAL RETURN ELECTRODE

(71) Applicant: Megadyne Medical Products, Inc., Draper, UT (US)

(72) Inventors: Michael D. Ehninger, South Jordan, UT (US); Paul R. Borgmeier, Salt Lake City, UT (US); Darcy W. Greep, Herriman, UT (US); Roger Millis, West Jordan, UT (US); Melissa K. Fischer, Cumming, GA (US)

(73) Assignee: Megadyne Medical Products, Inc., Draper, UT (US)

( * ) Notice: Subject to any disclaimer, the term of this patent is extended or adjusted under 35 U.S.C. 154(b) by 803 days.

This patent is subject to a terminal disclaimer.

(21) Appl. No.: 14/583,315

(22) Filed: Dec. 26, 2014

(65) Prior Publication Data

US 2015/0182280 A1   Jul. 2, 2015

Related U.S. Application Data

(63) Continuation-in-part of application No. 14/140,800, filed on Dec. 26, 2013.

(51) Int. Cl.
*A61B 18/12* (2006.01)
*A61B 18/16* (2006.01)

(52) U.S. Cl.
CPC .......... *A61B 18/1233* (2013.01); *A61B 18/16* (2013.01); *A61B 2018/167* (2013.01)

(58) Field of Classification Search
CPC ...... A61B 18/1233; A61B 18/16; A61N 1/04; A61N 1/0492

(Continued)

(56) References Cited

U.S. PATENT DOCUMENTS

| 3,089,496 A | 5/1963 | Degelman |
| 3,543,760 A | 12/1970 | Bolduc |

(Continued)

FOREIGN PATENT DOCUMENTS

| GB | 1480736 | 6/1973 |
| GB | 2052269 | 1/1981 |

(Continued)

OTHER PUBLICATIONS

Non-Final Office Action for U.S. Appl. No. 14/140,800 dated Apr. 22, 2016.

(Continued)

*Primary Examiner* — Linda Dvorak
*Assistant Examiner* — Ryan T Clark
(74) *Attorney, Agent, or Firm* — Workman Nydegger

(57) ABSTRACT

A self-limiting electrosurgical return electrode for use with electrosurgical procedures is disclosed. The return electrode includes a conductive element and pads disposed on opposing sides of the conductive element. The conductive element, optionally in combination with the pads, is configured to limit the density of electrical current that passes from a patient to the return electrode. The conductive element and the pads can cooperate to define two separate working surfaces on opposing sides of the return electrode. The return electrode can also be safely used with patients of substantially any size and without requiring adjustments to the power settings of an electrosurgical generator.

15 Claims, 9 Drawing Sheets

(58) Field of Classification Search
USPC .......................................................... 606/32
See application file for complete search history.

(56) References Cited

U.S. PATENT DOCUMENTS

| | | | |
|---|---|---|---|
| 3,601,126 A | 8/1971 | Estes | |
| 3,720,209 A | 3/1973 | Bolduc | |
| 3,848,600 A | 11/1974 | Patrick | |
| 4,088,133 A | 5/1978 | Twentier | |
| 4,092,985 A | 6/1978 | Kaufman | |
| 4,094,320 A | 6/1978 | Newton | |
| 4,117,846 A | 10/1978 | Williams | |
| 4,166,465 A | 9/1979 | Esty | |
| 4,188,927 A | 2/1980 | Harris | |
| 4,200,104 A | 4/1980 | Harris | |
| 4,207,904 A | 6/1980 | Greene | |
| 4,226,247 A | 10/1980 | Hauser | |
| 4,231,372 A | 11/1980 | Newton | |
| 4,237,886 A | 12/1980 | Sakurada | |
| 4,237,887 A | 12/1980 | Gonser | |
| 4,267,840 A | 5/1981 | Lazer | |
| 4,304,235 A | 12/1981 | Kaufman | |
| 4,384,582 A | 5/1983 | Watt | |
| 4,387,714 A | 6/1983 | Geddes | |
| 4,457,748 A * | 7/1984 | Lattin | A61N 1/0428 |
| | | | 600/573 |
| 4,669,468 A | 6/1987 | Cartmell | |
| 4,736,752 A * | 4/1988 | Munck | A61N 1/0452 |
| | | | 607/149 |
| 4,770,173 A | 9/1988 | Feucht | |
| 4,799,480 A | 1/1989 | Abraham | |
| 4,936,842 A | 6/1990 | D'Amelio | |
| 5,352,315 A | 10/1994 | Carrier | |
| 5,354,790 A | 10/1994 | Keusch | |
| 5,520,683 A | 5/1996 | Subramaniam | |
| 5,830,212 A | 11/1998 | Cartmell | |
| 5,836,942 A | 11/1998 | Netherly | |
| 6,049,927 A | 4/2000 | Thomas | |
| 6,053,910 A | 4/2000 | Fleenor | |
| 6,083,221 A | 7/2000 | Fleenor | |
| 6,111,233 A | 8/2000 | Rock | |
| 6,160,246 A | 12/2000 | Rock | |
| 6,214,000 B1 | 4/2001 | Fleenor | |
| 6,389,681 B1 | 5/2002 | Rock | |
| 6,454,764 B1 * | 9/2002 | Fleenor | A61B 18/08 |
| | | | 128/908 |
| 6,544,258 B2 | 4/2003 | Fleenor | |
| 6,547,786 B1 | 4/2003 | Globe | |
| 6,548,789 B1 | 4/2003 | Rock | |
| 6,582,424 B2 | 6/2003 | Fleenor | |
| 6,666,859 B1 | 12/2003 | Fleenor | |
| 6,713,733 B2 | 3/2004 | Kockman | |
| 6,723,967 B2 | 4/2004 | Rock | |
| 6,814,889 B1 | 11/2004 | O'Grady | |
| 6,852,856 B2 | 2/2005 | Rock | |
| 6,852,956 B2 | 2/2005 | Rock | |
| 6,875,963 B2 | 4/2005 | Rock | |
| 6,963,055 B2 | 11/2005 | Rock | |
| 7,038,177 B2 | 5/2006 | Rock | |
| 7,166,102 B2 | 1/2007 | Fleenor | |
| 7,202,443 B2 | 4/2007 | Rock | |
| 7,367,971 B2 | 5/2008 | Fleenor | |
| 8,876,812 B2 | 11/2014 | Aramayo | |
| 2001/0029367 A1 | 10/2001 | Fleenor | |
| 2003/0189037 A1 | 10/2003 | Kochman | |
| 2005/0101947 A1 | 5/2005 | Jarrard | |
| 2005/0113817 A1 * | 5/2005 | Isaacson | A61B 18/16 |
| | | | 606/32 |
| 2006/0074411 A1 | 4/2006 | Carmel | |
| 2008/0249521 A1 | 10/2008 | Dunning | |
| 2008/0249524 A1 | 10/2008 | Dunning | |
| 2009/0149852 A1 | 6/2009 | Eggers | |
| 2009/0171341 A1 | 7/2009 | Karl et al. | |
| 2009/0209953 A1 | 8/2009 | Schoenman | |
| 2010/0217260 A1 * | 8/2010 | Aramayo | A61B 18/16 |
| | | | 606/41 |
| 2015/0182278 A1 | 7/2015 | Ehninger | |

FOREIGN PATENT DOCUMENTS

| | | |
|---|---|---|
| JP | S55-168317 | 12/1980 |
| JP | S57-154409 | 9/1982 |
| JP | S57188250 | 11/1982 |
| JP | S6354148 | 3/1998 |
| TW | 200633334 | 9/2006 |
| TW | M442080 | 12/2012 |
| WO | 2008013459 | 1/2008 |

OTHER PUBLICATIONS

International Search Report and Written Opinion for PCT/US14/72426 dated May 29, 2015.
International Search Report and Opinion, PCT/US2010/024615 dated Apr. 26, 2010.
Wald, et al., "Accidental Burns Associated With Electrocautery," JAMA, Aug. 16, 1971, vol. 217, No. 7, pp. 916-921.
Office Action for U.S. Appl. No. 12/703,475 dated Nov. 23, 2012.
Office Action for U.S. Appl. No. 12/703,475 dated Apr. 16, 2013.
Office Action mailed U.S. Appl. No. 12/703,475 dated Aug. 30, 2013.
Notice of Allowance for U.S. Appl. No. 12/703,475 dated Jul. 11, 2014.
Supplementary European Search Report for application EP 14874779 dated Jul. 17, 2017.

* cited by examiner

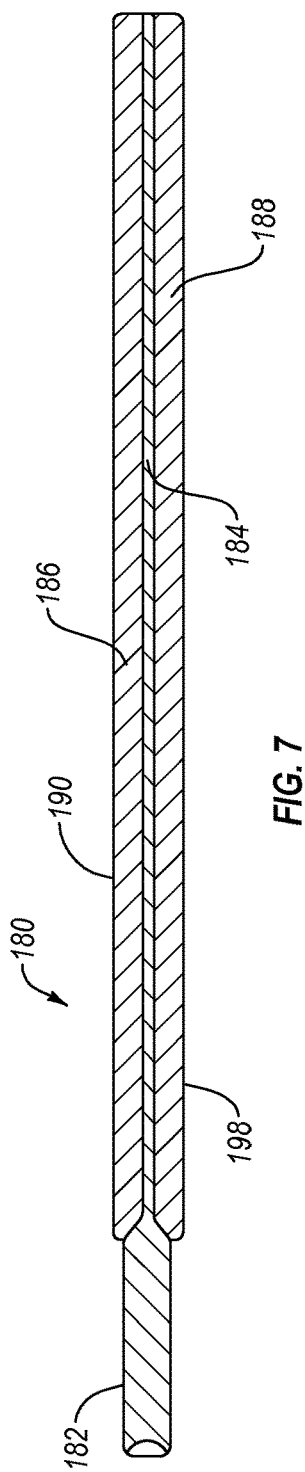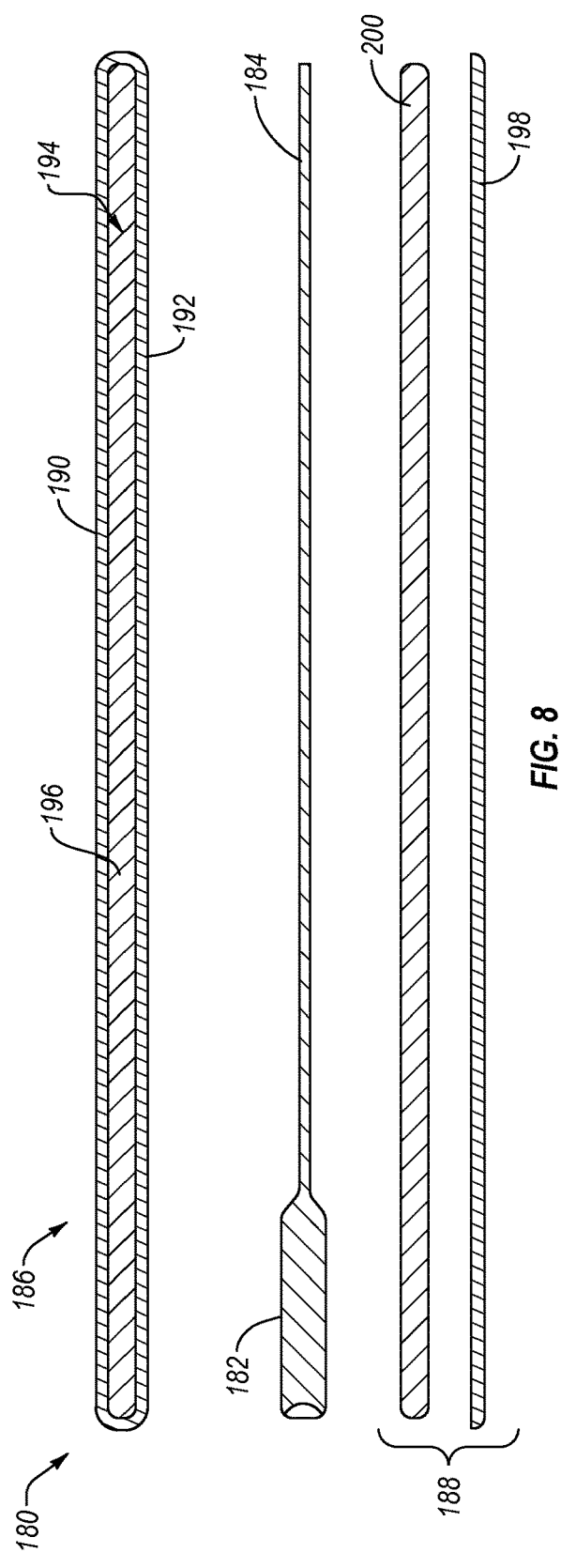
FIG. 7
FIG. 8

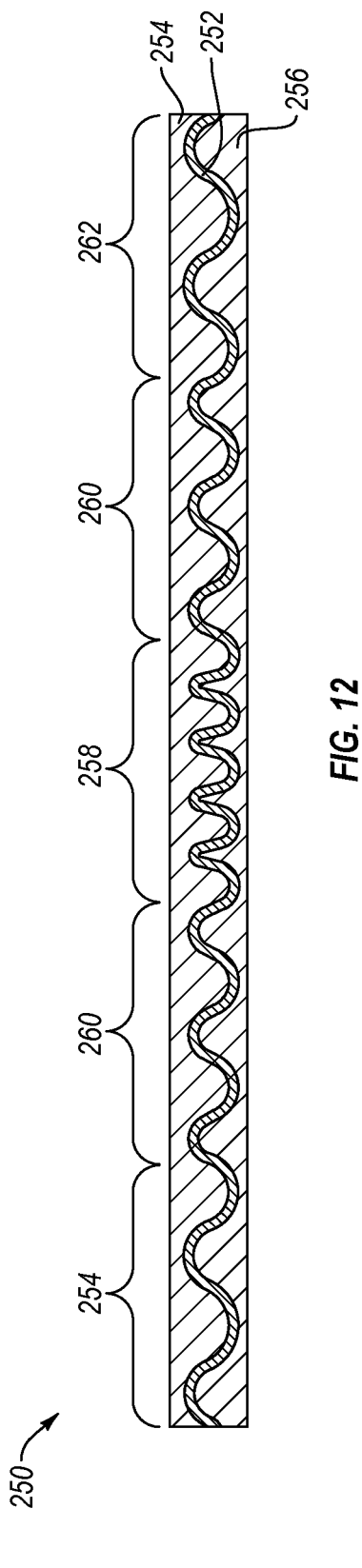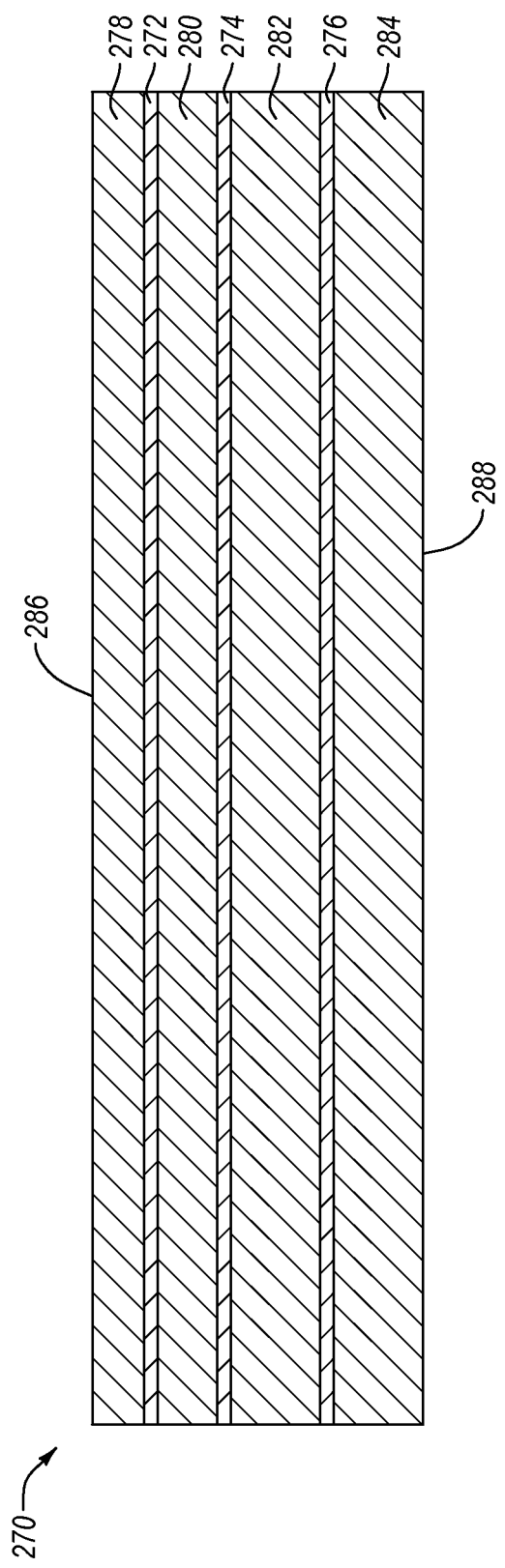

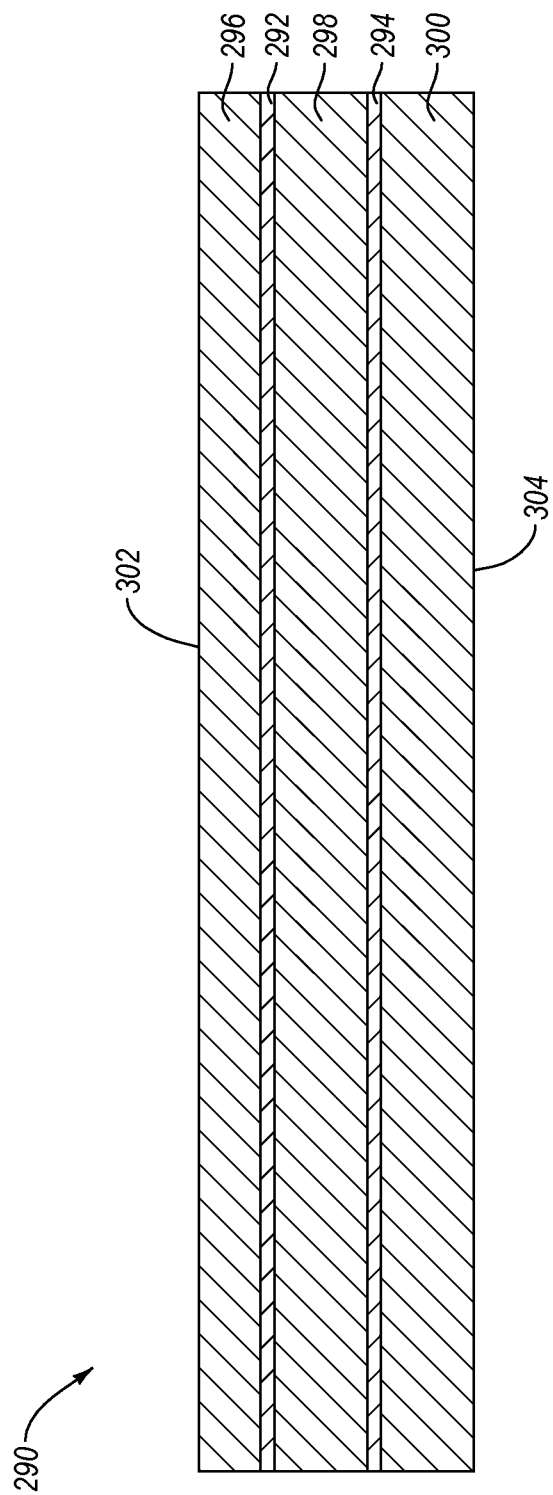

UNIVERSAL SELF-LIMITING ELECTROSURGICAL RETURN ELECTRODE

CROSS-REFERENCE TO RELATED APPLICATIONS

This application is a continuation-in-part of U.S. patent application Ser. No. 14/140,800, filed Dec. 26, 2013, entitled "UNIVERSAL SELF-LIMITING ELECTROSURGICAL RETURN ELECTRODE," the disclosure of which is incorporated herein by this reference.

BACKGROUND

1. Technical Field

The present disclosure relates generally to electrosurgical systems. In particular, the present disclosure relates to universal safety electrosurgical return electrodes that are adapted to be used with patients of substantially any size.

2. The Relevant Technology

In the area of electrosurgery, medical procedures of cutting tissue and/or cauterizing leaking blood vessels are performed by utilizing radio frequency (RF) electrical energy. As is known to those skilled in the medical arts, electrosurgery is widely used and offers many advantages including that of the use of a single surgical tool for both cutting and coagulation. The RF energy is produced by a wave generator or Electro-Surgical Unit (ESU) and transmitted to a patient's tissue through a hand-held electrode that is operated by a surgeon.

Monopolar electrosurgical generator systems have an active electrode that is applied by the surgeon to the patient at the surgical site to perform surgery and a return path from the patient back to the ESU. The active electrode at the point of contact with the patient must be small in size to produce a high current density in order to produce a surgical effect of cutting or coagulating tissue. The return electrode, which carries the same current as the active electrode, must be large enough in effective surface area at the point of communication with the patient such that a low density current flows from the patient to the return electrode. If a relatively high current density is produced at the return electrode, the temperature of the patient's skin and tissue will rise in this area and can result in an undesirable patient burn. According to the Emergency Care Research Institute, a well-known medical testing agency, the heating of body tissue to the threshold of necrosis occurs when the current density exceeds 100 milliamperes per square centimeter. Furthermore, the International Electrotechnical Commission ("IEC") has published standards that require that the maximum patient surface tissue temperature adjacent an electrosurgical return electrode shall not rise more than six degrees (6°) Celsius under stated test conditions.

Since the inception of electrosurgery, various types of return electrodes have been used. Initially, return electrodes consisted of flat stainless steel plates (which in later years were coated with a conductive gel) that were placed under the patient's buttocks, thigh, shoulders, or any location where gravity could ensure adequate contact area. Due to adjustments during a procedure, however, the contact area between the patient and the steel plate sometimes dropped below adequate levels. In such instances, the density of the current being transferred from the patient to the steel plate sometimes increased to levels that resulted in the patient being burned.

In an effort to improve the safety of return electrodes, the flat steel plates were eventually replaced with flexible return electrodes. Like the steel plate electrodes, the flexible return electrodes are also coated with a conductive or dielectric polymer. Additionally, the flexible return electrodes have an adhesive border on them so they can be attached to the patient without the aid of gravity. Because these flexible return electrodes are attached to the patients with an adhesive, these types of return electrodes are often referred to as "sticky pads." Upon completion of the electrosurgical procedure, these sticky pads are disposed of. Expectedly, the disposable nature of sticky pads has resulted in additional surgical costs in the United States of several tens of millions of dollars each year.

The use of sticky pads has resulted in fewer patient return electrode burns compared to the old steel plates. Nevertheless, hospitals still experience patient burns caused by sticky pads that accidentally fall off or partially separate from the patient during surgery. Furthermore, in order to achieve the reduced number of patient burns, the size and shape of the sticky pads have to match the available surface area of the patient.

For instance, if an adult sized sticky pad were used on a baby, parts of the sticky pad would not be in contact with the baby. As a result, the current density through the portion of the sticky pad that is in contact with the baby may increase to levels that cause burns on the baby. Additionally, the unattached portions of the sticky pad could also pose a burn risk to operating room personnel.

Additionally, due to the smaller surface areas of the sticky pads, the power settings on the ESU must be limited to control/limit the current density being transferred through the sticky pads. As a result, for instance, an infant sized sticky pad cannot be used on an adult patient because the required power settings to achieve the desired surgical effect cannot be used without the risk of causing a sticky pad site burn due to the small surface area.

In further attempts to alleviate the foregoing issues, standards (IEC 60601-2-25$^{th}$ Edition) have been established that divide patients in three weight ranges: less than 5 kg, 5 kg to 15 kg, and over 15 kg. Sticky pads have been made specifically sized to accommodate each weight range. Additionally, power setting limits have been established for sticky pads used in each weight range. Specifically, the IEC standards require that the electrosurgical current used with the sticky pads for the less than 5 kg weight category not exceed 350 milliamperes ("mA"). Similarly, the IEC standards require that the electrosurgical current used with the sticky pads for the 5 kg to 15 kg and the over 15 kg weight categories not exceed 500 mA and 700 mA, respectively.

As noted, larger sticky pads can only be safely used with patients that are large enough to provide sufficient surface area to make complete contact with the larger surface area of the sticky pads. Conversely, smaller sticky pads that are sized to make complete contact with smaller patients do not provide sufficient surface area to safely conduct current from larger patients at current densities below safe thresholds. Thus, regardless of whether the sticky pads are labeled for use with a specific patient size/weight range, the size and/or performance capabilities of individual sticky pads inherently restricts their safe use to patients within certain size/weight categories.

Subsequently, there was proposed a further improvement, an electrode contact quality monitoring system, which would monitor the contact area of the electrode in contact with the patient and turn off the electrosurgical generator whenever there was insufficient contact area. Such circuits are shown, for example, in U.S. Pat. No. 4,231,372, issued to Newton, and entitled "Safety Monitoring Circuit for Electrosurgical Unit," the disclosure of which is incorporated by this reference. This system has resulted in additional reduction in patient return electrode burns, but requires a special disposable electrode and an added circuit in the generator that drives the cost per procedure even higher. Additionally, these types of monitoring systems only provide a relative amount of safety. More specifically, such monitoring systems are controlled by human generated algorithms. In creating such algorithms, the algorithm creator must decide what parameters (e.g., contact area size, etc.) are considered safe. In use, however, the selected parameters may prove not to provide sufficient safety. Thus, the safety of such monitoring systems is only as good as the parameters selected for the algorithm in the monitoring system. In the first twenty years after this system was introduced, fewer than 40 percent of all the surgical operations performed in the United States used this system because of its high costs.

One of the biggest improvements to electrosurgery came in the form of self-limiting return electrodes. Unlike sticky pads and steel plate return electrodes, self-limiting return electrodes are relatively large, thereby eliminating the need for conductive gels that may irritate a patient's skin. Additionally, self-limiting return electrodes typically employ geometries and materials whose impedance characteristics, at typically used electrosurgical frequencies, are such that the return electrode self-limits current densities (and corresponding temperature rises) to safe thresholds, should the contact area between the patient and the electrode be reduced below otherwise desirable levels. Furthermore, self-limiting return electrodes were specifically designed to evenly distribute the current density over the entire contact area between the patient and the return electrode in order to reduce the risk of patient burns.

While the use of self-limiting return electrodes has even more dramatically reduced the number of patient burns experienced during electrosurgical procedures, typical self-limiting return electrodes still suffer from some limitations. For instance, like sticky pads, typical self-limiting return electrodes are commonly made in multiple sizes for different sized patients. For instance, a typical self-limiting return electrode for a relatively small person (e.g., under 50 lbs) may be about 26×12 inches while a typical self-limiting return electrode for a larger person may be about 46×20 inches.

Furthermore, typical self-limiting return electrodes are often asymmetrical in their construction such that only one surface of the electrode can be used as a working surface. As a result, operating room personnel must take care to ensure that the return electrode is positioned on the operating room table with the proper surface facing upward toward the patient. If the working surface is not positioned towards the patient, there may be insufficient capacitive coupling between the patient and the return electrode for the return electrode to function properly.

The asymmetrical nature of the construction is often due to the inclusion of additional or thicker layers of materials (e.g., dielectric, cushioning, etc.) on one side of a conductive element than on another side. Not only does the asymmetrical construction of typical self-limiting return electrodes limit which surfaces can be used as working surfaces, the thickness of some of the layers can limit the ability of the return electrode to work across different categories of patients. For instance, a self-limiting return electrode that works for an adult may not provide sufficient coupling for an infant because a cushion layer is too thick.

Thus, although various advances have been made in the electrosurgical arts, there remains room for improvement. More particularly, while systems and devices have been developed to increase the safety of patients undergoing electrosurgical procedures, such as by reducing the number of patient return electrode burns, the versatility of return electrodes has remained an issue. In particular, as noted above, previous return electrodes have needed to be tailored to different categories of patients (typically size or weight categories) and have been limited in the particular manner of use (e.g., current levels, orientation of working surface, etc.).

Therefore, it would be an advance in the present electrosurgical art to provide a universal safety electrosurgical return electrode that is self-limiting and that can be used across all categories of patients and in more versatile ways.

BRIEF SUMMARY

The present disclosure addresses the foregoing shortcomings by providing a self-limiting return electrode that can be safely used with essentially any patient, regardless of size or weight, and that is more symmetrical such that multiple surfaces of the return electrode function as working surfaces.

Briefly, return electrodes according to the disclosed embodiments include a relatively large effective surface area compared to sticky pads and steel plate return electrodes. It is so large and so adapted for positioning relative to the body of a patient that it eliminates the need for conductive gels. Moreover, the exposed surface is of a material that is readily washable, disinfectable, and/or sterilizable so as to facilitate easy and rapid conditioning for repeated use. It employs geometries and materials whose impedance characteristics, at typically used electrosurgical frequencies, are such that it self-limits current densities (and corresponding temperature rises) to safe thresholds, should the effective contact area between the patient and the working surface of the electrode be reduced below otherwise desirable levels. Accordingly, the need for the foregoing expensive and only relatively safe monitoring circuits in specialized RF generators is eliminated.

In accordance with some embodiments, an electrosurgical return electrode is made sufficiently large to present sufficiently low electrical impedance and low current densities at typical electrosurgical frequencies used in medical procedures to reduce the possibility of excessive temperature elevation in adjacent patient tissue, (i.e., by maintaining temperature ("T") rise below six degrees (6°) Celsius) thereby avoiding tissue necrosis or other undesired patient trauma.

In accordance with some embodiments, the return electrode can have a substantially symmetrical construction such that opposing major surfaces of the return electrode can each function as a working surface (the surface of the return electrode that is in contact with or in close proximity to the patient during a procedure). Furthermore, each working surface of the return electrode is made sufficiently large in area so that in normal use, current flow will not be reduced to a point where it impedes the surgeon's ability to perform surgery at the surgical site.

In accordance with some embodiments of the present disclosure, the return electrode can be used across wide categories of patients. For instance, a return electrode according to some embodiments can be used on patients of substantially any weight. Similarly, a return electrode according to some embodiments can be used on patients that weight 0.8 lb or more. According to still other embodiments, a return electrode can be used on patients from multiple weight categories as defined by industry standards (e.g., IEC). For instance, a single return electrode can be used on any patient regardless of whether that patient falls within the less than 5 kg category, the 5 kg to 15 kg category, or the above 15 kg category.

In accordance with some embodiments, a universal safety return electrode self-limits current densities (and corresponding temperature rises) to safe thresholds while the current density across the contact area between the patient and the return electrode are non-uniform. The non-uniform current density distribution can enable the return electrode to be used with patients of substantially any size while still providing the self-limiting features discussed herein.

In accordance with some embodiments, controlled electrical conductivity is imparted to the electrode by the inclusion therein of electrically conductive materials such as conductive threads or carbon black, thus conditioning conductivity as a function of surface area to levels which limit passage of current therethrough to safe values.

In accordance with some embodiments, the electrical impedance of the materials in and adjacent to the working surface of the electrode is sufficiently elevated so as to limit current density at the working surfaces to a level below the threshold of patient tissue trauma, thus providing a self-limiting characteristic to prevent patient trauma in the event of accidental reduction of the effective working surface of the electrode.

Additional features and advantages of the disclosed embodiments will be set forth in the description which follows, and in part will be obvious from the description, or may be learned by the practice of the disclosure. These and other features will become more fully apparent from the following description and appended claims, or may be learned by the practice of the present disclosure.

BRIEF DESCRIPTION OF THE DRAWINGS

To further clarify the above and other advantages and features of the present disclosure, a more particular description will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 7 is a simplified cross section taken along the lines 7-7 of FIG. 6;

FIG. 8 is a simplified exploded cross section of the electrosurgical return electrode of FIG. 6;

FIG. 12 is a simplified cross section of an electrosurgical return electrode according to the present disclosure;

FIG. 13 is a simplified cross section of another electrosurgical return electrode according to the present disclosure;

FIG. 14 is a simplified cross section of still another electrosurgical return electrode according to the present disclosure.

DETAILED DESCRIPTION

The electrosurgical return electrodes disclosed herein employ geometries and materials whose impedance characteristics, at typically used electrosurgical frequencies, are such that they self-limit current densities (and corresponding temperature rises) to safe thresholds, should the contact area between a patient and an effective working surface of the electrode be reduced below otherwise desirable levels. Additionally, the disclosed self-limiting electrosurgical electrodes are capable of being used with patients of substantially any weight or size. Accordingly, the return electrodes disclosed herein may be referred to as "universal safety return electrodes" or "universal self-limiting return electrodes." Furthermore, some of the disclosed self-limiting electrosurgical electrodes have a substantially symmetrical construction such that the electrodes have two major surfaces that can be used as effective working surfaces.

FIGS. 1-14 and the corresponding discussion relate to the structures and features of universal safety electrosurgical electrodes that provide self-limiting characteristics and that can be used with patients of substantially any size. Previous self-limiting return electrodes were designed based on the assumption that patients are purely (and uniformly) conductive. Accordingly, previous self-limiting return electrodes were designed to uniformly distribute the electrosurgical current over the entire contact area between a patient and an effective working surface of the electrode. In contrast, the embodiments and discussion provided in connection with FIGS. 1-14 are based on the understanding that patients are both (non-uniformly) conductive and resistive (e.g., some tissue is conductive and some tissue is resistive), not purely or uniformly conductive. Included in such discussion is a detailed description of illustrative embodiments of universal self-limiting return electrodes that can be used with substantially any sized patient.

Figure 1:
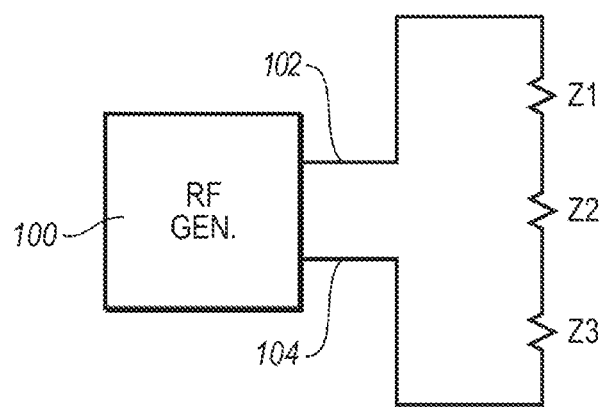
FIG. 1 is a simplified electrical schematic diagram illustrating typical impedances effectively included in the operative path of radio frequency current flow as presented to an electrosurgical generator during an operative procedure.
Figure 2A:
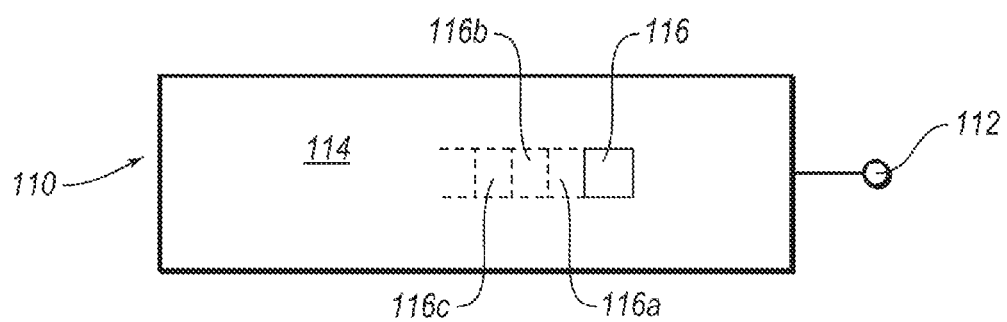
FIG. 2A is a top view of a wide-area distributed electrosurgical return electrode illustrating the principles of the disclosure.
Figure 2B:
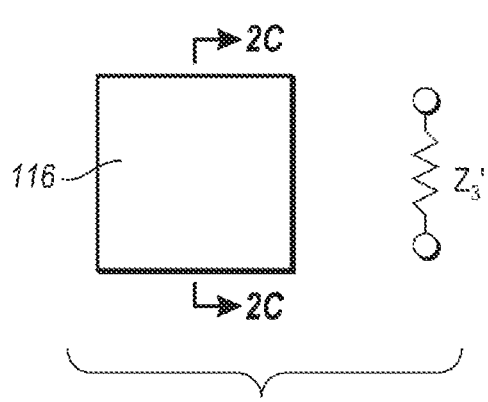
FIG. 2B is an enlargement of a segment of the electrosurgical return electrode of FIG. 2A.
Figure 2C:
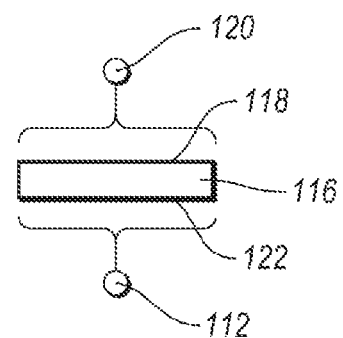
FIG. 2C is a cross section taken along the section lines 2C-2C of FIG. 2B and illustrating the effective circuit impedance represented by the segment of 2B.
Figure 3:
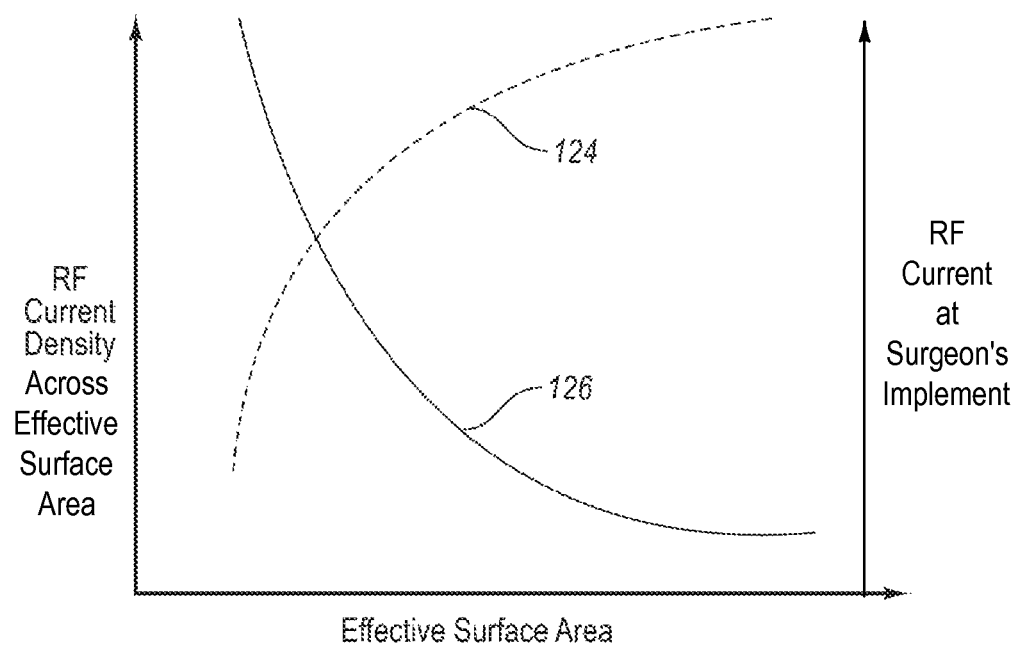
FIG. 3 is a chart illustrating in graphical form the relationships between effective surface area of the return electrode and the effective radio frequency current density developed at the electrode.

Now turning to the drawings, and more particularly to FIGS. 1-3, a general discussion of self-limiting return electrodes and the general principles by which they operate will be provided. FIG. 1 thereof depicts a simplified electrical schematic diagram illustrating typical impedances effectively included in the operative path of radio frequency current flow as presented to an electrosurgical generator during an operative procedure. There, it will be seen are conventional radio frequency electrical power generator 100, such as but not limited to constant power, voltage, and/or current or variable power, voltage and/or current generators. Connected to electrical power generator 100 are conventional electrical conductors 102 and 104 which respectively connect generator 100 to the surgeon's implement represented by impedance $z_1$ and an electrosurgical return electrode represented by impedance $z_3$. Impedance $z_2$ is provided to represent the impedance presented by the patient's tissue lying between the operation site and the return electrode. Electrical conductors 102 and 104 are representative of one illustrative structure that is capable of performing the function of connecting means for making electrical connection to the return electrode. It may be appreciated by one skilled in the art, however, that various other structures are appropriate and capable of performing the desired function.

Although the diagram of FIG. 1 is simplified and generally considers circuit elements in terms of the principal resistances, including the reactance contributed by the surgical instrument, the patient's body and the return electrode, so as to clearly and succinctly illustrate principles of the disclosure, it should be understood that in reality certain other parameters would be encountered, parameters such as distributed inductance and distributed capacitance which, for purposes of clarity in illustration of the principles hereof, are deemed relatively small and so not considered at this point in this description. However, as set forth below, in one embodiment when an insulating sleeve is interposed between the electrode and the body of a patient, a significant element of capacitive reactance may be included in the impedance of $z_3$. It should also be noted that the Figures are intentionally simplified so as to present the principles of the disclosure succinctly.

The initial embodiment, hereof, is that of an electrode operating in a combined resistive and/or capacitive mode. Accordingly, if the relatively small stray capacitive and inductive reactances are disregarded, the total effective impedance of the circuit will be equal to the sum of the individual impedances $z_1$, $z_2$ and $z_3$; and since essentially the same current will pass through all three, the voltage generated by RF generator 100 will be distributed across impedances $z_1$, $z_2$, and $z_3$ in direct proportion to their respective values. Thus, the surgical energy stored in each of such components will also be directly proportional to their values.

Since it is desired that developed energy be concentrated in the region where the surgeon's implement contacts the patient's tissue, it is desirable that the resistive component of the impedance represented by $z_1$ be substantial and that current passing therethrough be concentrated in a very small region. The latter is accomplished by making the region of contact with the patient at the operative site very small.

It is known that, in contrast with the foregoing series circuit, components of combined resistive and capacitive reactance, when connected in parallel, present a total effective impedance that is given by the formula:

$$z_{eff} = \frac{1}{\frac{1}{z_1} + \frac{1}{z_2} + \frac{1}{z_3} + \frac{1}{z_4} + \frac{1}{z_5} + \frac{1}{z_6} \ldots} \quad (1)$$

Thus, if 100 similar impedances, each of 100 ohms, were connected in parallel, the effective impedance $Z_{eff}$ would equal one ohm. If half of such impedances were effectively disconnected, the remaining effective impedance would be two ohms, and if only one of the impedances were active in the circuit, the remaining effective impedance would be 100 ohms. The significance of these considerations and their employment to render the electrode self-limiting and fail-safe will be evident from the following description of the elements illustrated in FIGS. 2A, 2B, 2C, and 3.

Now turning to FIG. 2A, there will be seen a schematic representation of the top view of a wide-area distributed electrosurgical return electrode 110 illustrating some principles of the disclosure. At the right hand side of the figure there is shown an electrical connection terminal 112 to facilitate connection to an electrical return conductor, such as conductor 104 of FIG. 1. The surface 114 of return electrode 110 is preferably smooth and homogeneous and includes a thin resistive and/or dielectric layer. Alternatively, surface 114 of return electrode 110 may include a capacitive and/or inductive layer, depending on the particular operation of return electrode 110. For instructional purposes of this description and to aid in the mathematical modeling of return electrode 110, electrode 110 may be thought of as including a plurality of uniformly-sized regions or segments as represented by regions 116, 116a, 116b, 116c . . . 116n. It will be appreciated by one skilled in the art, however, that return electrode 110 may or may not include discontinuous regions or segment, it being preferred that electrode 110 have continuous segments.

Region/segment 116 is shown larger in FIG. 2B in order to be similar in scale to the resistive impedance $z_3'$ it represents. It thus will now be evident that each of the segments of electrode 110 corresponding to segments 116 . . . 116n inherently has the capability of presenting an impedance similar to that of impedance $z_3'$. In some embodiments, the impedances presented by each of the segments of electrode 110 may be equal or substantially equal to one another. In other embodiments, however, the impedances presented by the segments of electrode 110 may not be equal or substantially equal to one another. The variations in the impedances presented by the segments of electrode 110 and/or the variations in the conductivity of patient tissue can contribute to the non-uniform distribution of electrosurgical current density between the patient and the return electrode.

In contrast to prior self-limiting return electrodes that required uniform current distribution, the return electrodes of the present disclosure do not require that the electrosurgical current be uniformly distributed over the entire contact area between the patient and the return electrode. Rather, the return electrodes of the present disclosure are specifically designed to allow for the non-uniform distribution of the electrosurgical current across the contact area between the patient and the return electrode. In other words, the return electrodes of the present disclosure are designed to maximize current density (while still providing the self-limiting characteristics) by minimizing the effective surface area between the patient and the return electrode that is used to conduct the electrosurgical current. Such non-uniform distribution of the electrosurgical current is one feature of the present return electrodes that allows for the present return electrodes to be safely used with patients of substantially any size and across multiple patient weight categories.

More specifically, with prior uniform-distributing self-limiting return electrodes, the effective surface area (i.e., the contact area used to conduct current between the patient and the return electrode) would be equal to the total contact area between the patient and the return electrode. In contrast, the return electrodes of the present disclosure can allow for an effective surface area to be the same as or smaller than the total contact area between the patient and the return electrode.

Thus, for instance, while a large supine patient may make contact with a large portion of the upper surface of a return electrode of the present disclosure, the effective surface area may be substantially smaller than the total contact area. In other words, the return electrodes of the present disclosure may allow for a significant portion of the electrosurgical current to be concentrated in an area that is substantially smaller than the total contact area between the patient and the return electrode while still limiting the current density to safe levels. In the case of a small patient, such as an infant, that total contact area and the effective surface area may be substantially the same. Thus, regardless of whether the patient is large or small, a relatively small portion of the surface of the return electrode may be used to effectively and safely conduct electrosurgical current.

The number of segments $116 \ldots 116n$ which are active in parallel within the circuit can be a function of the effective surface area between the patient and the electrode. Thus, the segments corresponding to segments $116 \ldots 116n$ within the effective surface area could be paralleled in the circuit to form an impedance represented by impedance $z_3$ of FIG. 1. As long as the effective surface area is sufficiently large (e.g., enough segments $116 \ldots 116n$ are paralleled in the circuit), the current density and temperature elevation are maintained below the danger thresholds mentioned above.

Now, if for any reason, the effective surface area between the patient and electrode were to be reduced to the surface of only one of the segments $116 \ldots 116n$, then the effective impedance (combined capacitive reactance and resistance in the example under consideration) would substantially increase; and at some point of reduction in effective surface area, the effective impedance would rise to a level relative to the impedance presented at the site of the electrosurgical instrument so as to diminish the electrosurgical effect of the surgical instrument or otherwise prevent effective use of the instrument by the surgeon, thus signaling the surgeon that the patient should be repositioned so as to present a greater effective surface area with the return electrode. At the same time, the total circuit impedance would be increased so that the total current that would flow if the surgeon attempted to employ his instrument without repositioning the patient would be reduced to a value below that which would cause undesired trauma to the patient. Accordingly, there is provided a self-limiting feature that enhances safety in use (through the natural characteristics of the return electrode) without the need for the aforementioned separate circuit monitoring and control circuits, with their human generated algorithms that only provide a relative level of safety.

FIG. 2C is a cross section taken along the section lines 2C-2C of FIG. 2B and illustrates the effective circuit impedance $z_3$ represented by the segment 116 of 2B. There, in FIG. 2C is seen small segment 116 with its upper patient-contacting surface 118 represented electrically by terminal 120 and its lower surface 122 represented by electrical terminal 112. For the purpose of this description (and in order to present the principles underlying this embodiment clearly), the impedance $z_3$ may be thought of as existing between terminals 120 and 112. Of course, it will be evident to those skilled in the art that in an embodiment in which a thin but highly conductive layer is included along the lower surface of electrode 110, each of the impedances represented by the remaining segments are connected at their lower extremities in parallel to terminal 112; whereas, if such highly conductive layer is absent, then, in addition to the impedance represented by the material lying between the upper and lower regions of each segment, there will be an additional impedance (not shown) that is represented by the material through which current would have to pass transversely or laterally through the electrode in order to get to terminal 112.

It should now be evident that if lateral impedance is minimized by provision of the aforementioned thin conducting layer, or if the effective conductivity at the lower part of the material of region 116 is otherwise increased, the effective impedance presented by the return electrode will be inversely proportional to the effective upper surface of the electrode that is in contact with a patient.

FIG. 3 is a chart generally illustrating in graphic form the relationships between the effective surface area of the return electrode and (i) the effective radio frequency current densities developed at the electrode and (ii) the radio frequency current available at the surgeon's implement. However, before proceeding to a consideration of such chart, it should be noted that the chart is simplified so as to illustrate the principles underlying the disclosure and does not represent actual data, which may vary substantially. For instance, it will be understood that the scale of the current density across the effective surface area shown on the y-axis on the left side of the chart will be different (and the value will be much lower) than the scale of the current available at the surgeon's implement shown on the y-axis on the right side of the chart.

In FIG. 3 there is seen a plot of RF Current Density versus Electrode Effective Surface Area, the latter (as should now be evident to those skilled in the art) being that part of the surface of the return electrode that makes effective electrical contact with the body of a patient. As would be expected from the foregoing discussion, when the effective area is large, the current at the surgeon's implement is high (dashed graph line 124) and the corresponding current density across the return electrode is very low (solid graph line 126). This is, of course, the condition desired for conducting electrosurgery. However, if we assume constant current throughout the circuit, as the effective surface area decreases, the current density across the return electrode (solid graph line 126) increases with a corresponding decrease in the current at the surgeon's instrument (dashed graph line 124). When the effective surface area declines to some predetermined point, there will remain insufficient current at the surgical instrument to effectively conduct electrosurgery.

It may be appreciated by one skilled in the art that the change in current density and available current to the surgeon may or may not occur simultaneously with the variations in effective surface area. Various embodiments of the present disclosure may have substantially simultaneous changes in current density and available current, while other embodiments of the present disclosure may include a lag period therebetween.

The parameters selected for the materials and electrode dimensions are chosen so that current density and corresponding tissue temperature elevation adjacent the return electrode do not exceed the limits mentioned elsewhere herein. It will now be seen that by a proper selection of such parameters the return electrode is made self-limiting, thereby obviating the need for the additional monitoring circuits to which reference is made above.

To facilitate description of the principles underlying the disclosure, the foregoing is described in terms of impedances whose principal components are resistances and capacitive reactances. However, the principles of the disclosure are also applicable to other embodiments in which the impedances include any combination of resistive, capacitive and/or inductive impedances.

The disclosure hereof is now further described in connection with applications in which an effective dielectric layer is represented by, for example: (i) a physical dielectric layer on the upper surface of the electrode; (ii) the material of a surgical gown worn by the patient; (iii) a bed sheet or other operating room linens interposed between the patient and the return electrode; (iv) the material of a protective sleeve fitted over the return electrode; (v) or any combination thereof.

Figure 4:
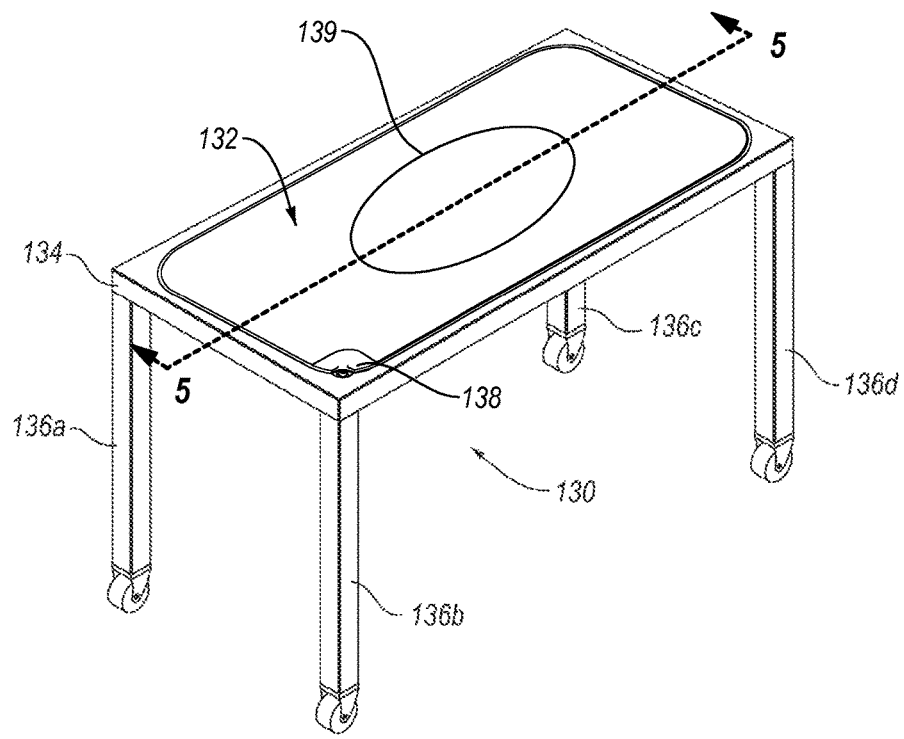
FIG. 4 is a perspective view showing an operating table with an electrosurgical return electrode according to the present disclosure disposed on the upper surface thereof.
Figure 5:
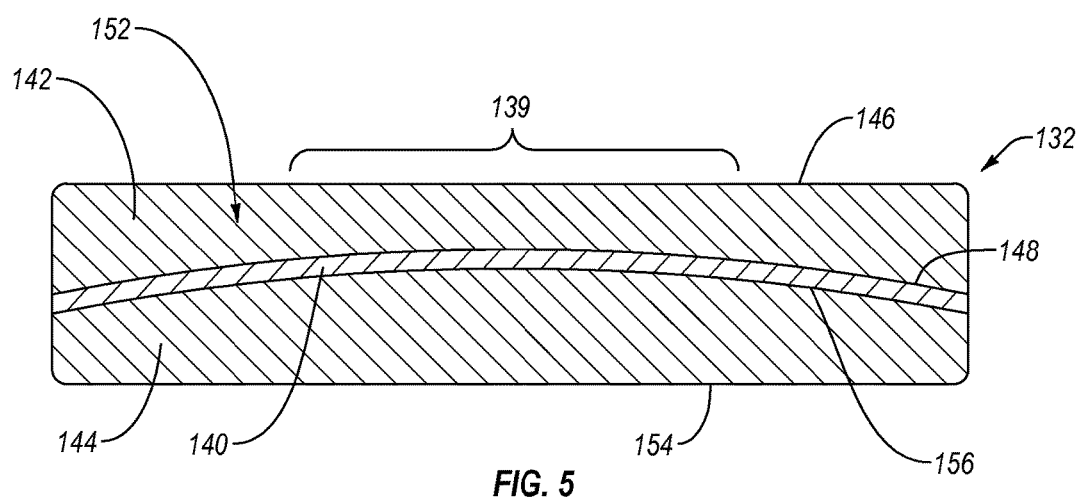
FIG. 5 is a simplified cross section taken along the lines 5-5 of FIG. 4.

Reference is now made to FIGS. 4-5, which illustrate an electrosurgical return electrode 132 according to the present disclosure. In FIG. 4, electrosurgical return electrode 132 is shown in perspective on operating table 130 with electrosurgical return electrode 132 according to the present disclosure disposed on the upper surface thereof, an edge of table 130 being identified by reference number 134. Operating table 130 is shown to have conventional legs 136a-136d that may be fitted with wheels or rollers as shown. Table 130 is one structure that is capable of performing the function of supporting means for supporting a patient during treatment. It may be appreciated by one skilled in the art, however, that various other configurations of support means are possible and capable of performing the required function. For example, supporting means may include but not be limited to chairs, plates, beds, carts, and the like.

Although, in FIG. 4, the entire upper surface of table 130 is shown as being covered with return electrode 132, it should be understood that entire coverage is by no means required in order to practice the principles of the disclosure. Thus, when used with conventional electrosurgical generators, the return electrode needs only to present an effective working surface area which is sufficient to provide adequate resistive, capacitive, or inductive coupling at the typically employed RF frequencies so as not to interfere with the surgeon's ability to perform surgery while at the same time avoiding undesired tissue damage. It has been found that at conventional electrosurgical frequencies, this has necessitated only an effective working surface area no larger than about the projected outline of one-third of the torso for an adult patient lying on an operating table or a portion of the buttocks of a patient sitting in a chair. However, the effective working surface area will vary depending on the material used, in some geometrical configurations, and in instances where various layers of operating room linens are placed over the electrode. The principles hereof may be successfully employed and the effective working surface area of the return electrode determined in such circumstances by routine experimentation. Under certain conditions, the effective working surface may be as small as about seven square inches (or about 45 square centimeters).

Moreover, although return electrode 132 shown in FIGS. 4-5 is depicted as being rectangular in shape, it will be evident that return electrodes according to the present disclosure could be oval or contoured as, for example, to follow the silhouette of the at least a portion of the torso or other principal part of the body of a patient. As will be evident from the foregoing, it is important that the electrode be configured so that when the electrode is used: (1) the return current density on the surface of the patient is sufficiently low; (2) the electrical impedance between the electrode and the patient is sufficiently low so that electrical energy is not concentrated sufficiently to heat the skin of the patient at any location in the electrical return path by more than six degrees (6°) Celsius; and (3) the characteristics of the materials and geometries are such that if the effective surface area is reduced below a selected threshold level, there will be insufficient energy dissipated at the surgeon's implement for him to continue effectively using the implement in its electrosurgical mode.

As will be recognized by those skilled in the art, it is not necessary for there to be direct ohmic contact between the skin of a patient and the return electrode hereof for the electrode to perform generally according the foregoing description, for although capacitive reactance (represented by the distance between a patient's body and the electrode) will be introduced if something such as a surgical gown separates them, such capacitive reactance will modify rather than destroy the impedance identified as $z_3$.

Those skilled in the art know that, with the currently used disposable return electrodes, reducing the effective size of the electrode to about three square inches will not reduce the RF current flow to a level where it will impede the surgeon's ability to perform surgery nor concentrate current to a level to cause patient trauma. However, to provide for some spacing of the electrode from patient's body, a return electrode according to the present disclosure, may need a minimum effective surface area of between about 7 and about 11 square inches (about 45 $cm^2$ to about 70 $cm^2$) with a relatively small separation from the skin of the patient such as that provided by a surgical gown or no interposing gown at all. Such an effective surface area is easy to obtain if the patient is positioned on an electrode that is the size of at least a portion of their upper torso or larger.

The characteristics of the desired dielectric for the present embodiment are sufficiently comparable to those of selected rubbers, plastics and other related materials that the latter may be satisfactorily employed as materials for the return electrode. As mentioned above, with such a return electrode, if the patient is positioned such that not enough of the return electrode is in close proximity to the patient to result in as low impedance as needed, the results would be that the current flow from the electrosurgical generator would be reduced to a level making it difficult for the surgeon to perform surgery. Thus, in the present embodiment, notwithstanding interposition of some additional capacitance represented by a surgical gown, the features described above will continue to occur.

It will be observed that when return electrode 132 is laid out on operating table 130, the upper exposed, or working, surface of the electrode again is expansive so as to meet the foregoing criteria for low impedance. Although it is not necessary that the electrode cover the entire surface of an operating table or the entire seat surface of a dental or other patient chair, it has been found advantageous in some instances to provide a greater surface area than that of the projected area of a portion of the buttocks or torso of a patient so that if a patient position shifts during the course of a procedure, a sufficient portion of the patient will remain in registration with the electrode surface so that the effective impedance will remain less than the above-described level.

At this juncture, it may be helpful to emphasize characteristics of the improved electrode according to the disclosure hereof that are deemed particularly relevant to an understanding of the operative character thereof. First, as mentioned above, the electrode does not need to be in direct contact with a patient, either directly or through intervening conductive or nonconductive gel. In addition, because of its expansive size, there is no need for tailoring the electrode to fit physical contours of a patient. While it has been found that with selected materials and geometries, the self-correcting and self-limiting principles hereof could be achieved in an electrode as small as about seven square inches (or about 45 square centimeters) in working surface area, the preferable range of exposed upper working surface area of the electrode lies in the range of from about 11 to 1,500 square inches (or about 70 to 9,680 square centimeters). By making the electrode several times larger (typically, at least an order of magnitude larger) in working surface area than steel plates or sticky pads, the need for direct physical attachment, either directly to the skin of the patient or through gels, is eliminated.

Return electrode 132, as illustrated in FIGS. 4-5, may be made of conductive plastic, rubber, or other flexible material which, when employed in the electrode will result in an effective dc resistance presented by each square centimeter of working surface to be greater than about 8000Ω or alternatively provide a bulk impedance of greater than 4000 Ω·cm. Silicone, butyl rubber, or urethane has been found to be particularly attractive materials as they are flexible, as well as readily washable and sterilizable. Alternatively, the main body of the return electrode may be made of inherently relatively high resistance flexible material altered to provide the requisite conductivity. A preferred example of the latter is that of silicone rubber material in which there are impregnated conductive fibers, such as carbon fiber, or in which there have been distributed quantities of other conductive substances such as carbon black, quantities of gold, silver, nickel, copper, steel, iron, stainless steel, brass, aluminum, or other conductors.

Further reference to FIG. 4 reveals the presence of a conventional electrical connector 138 attached to return electrode 132 to provide a conventional electrical return to the electrosurgical radio frequency energy source (not shown). Connector 138 is another structure capable of performing the function of connecting means for making electrical connection to the return electrode. Connector 138 is only illustrative of one possible structure for performing the desired function; it being appreciated by one skilled in the art that various other structures are capable of performing the required function.

FIG. 4 also illustrates that return electrode 132 includes an area 139. Area 139 of return electrode 132 may be adapted to have smaller patients positioned thereon. For instance, area 139 may be sized to have an infant sized patient positioned thereon. Furthermore, as discussed in greater detail below, return electrode 132, and particularly area 139 thereof, may be configured to provide the self-limiting characteristics discussed herein for infant sized patients positioned on area 139.

Although not illustrated, return electrode may also include additional areas configured to provide self-limiting characteristics for patients from different industry standard weight categories. By way of non-limiting example, area 139 may be configured to provide self-limiting characteristics for patients under 5 kg, a second area may be configured to provide self-limiting characteristics for patients between 5 kg and 15 kg, and a third area may be configured to provide self-limiting characteristics for patients over 15 kg. In some embodiments the areas for different sized patients may overlap one another, while in other embodiments the areas do not overlap. Furthermore, the areas may be formed concentrically with one another.

Regardless of the specific arrangement of areas for different sized patients (e.g., non-overlapping, overlapping, concentric, etc.) return electrode 132 may include one or more visual indicators to identify the areas for different sized patients. For instance, area 139 may include a visual indicator that identifies area 139 as suitable for patients under 5 kg. Similarly, a second area may include a visual indicator that identifies the second area as suitable for patients between 5 kg and 15 kg, and a third area may include a visual indicator that identifies the third area as suitable for patients over 15 kg. The one or more visual indicators may include labels, outlines, pictures, or other indicia that are printed or otherwise displayed on the outside surface(s) of return electrode 132. The one or more visual indicators may also or alternatively take the form of color coding. For example, each area of return electrode 132 may have a different color. The colors may be printed on return electrode 132 or the colors may be integrated into other components of return electrode 132. For instance, one or more components within area 139 may have a first color while one or more components in the other area(s) may have different colors so that the areas are distinguishable from one another.

Attention is now directed to FIG. 5, which illustrates a simplified section taken along the lines 5-5 of FIG. 4. As illustrated in FIG. 5, return electrode 132 includes a conductive element 140 and pads 142, 144 on opposing sides of conductive element 140. Conductive element 140, in one configuration, is made of a conductive plastic, rubber or other flexible material which, when employed as a conductive element, will result in an effective DC resistance presented by each square centimeter of the working surface of return electrode 132 (the surface that is in contact with or in close proximity to the patient) to be greater than about 8000 ohms or alternatively provide a bulk impedance of greater than 4000 Ω·cm. Various materials may be appropriate to give the required impedance. For example, silicone, butyl rubber, or urethane have been found to be particularly attractive materials for conductive element 140 as they are flexible, as well as readily washable, disinfectable, and sterilizable. Alternatively, in another embodiment, conductive element 140 may be made of an inherently relatively high resistance flexible material altered to provide the requisite conductivity. One example of the latter is that of silicone rubber material in which there are impregnated conductive fibers, such as carbon black, quantities of gold, silver, nickel, copper, steel, iron, stainless steel, brass, aluminum, or other conductors.

In some embodiments, conductive element 140 may be fabricated from a material that is substantially transparent to one or more wavelengths of electromagnetic radiation, such as but not limited to, microwave radiation, infra-red (IR) radiation, ultraviolet (UV) radiation, X-ray radiation, radio frequency (RF), and the like. This allows conductive element 140 and return electrode 132, when the other components of return electrode 132 are transparent to one or more wavelengths of electromagnetic radiation, to be maintained in place during performance of certain medical procedures using particular wavelengths of electromagnetic radiation.

It may be appreciated by one skilled in the art that conductive element 140 may have various other configurations so long as conductive element 140 is capable of performing the functions of an electrode, i.e., being capable of passing current therethrough. For example, in some embodiments, conductive element 140 includes a thin, highly conductive lower stratum that facilitates connection of return electrode 132 to an electrosurgical radio frequency energy source (not shown). In another alternate embodiment, conductive element 140 is configured from multiple layers of conductors. In still yet another embodiment, conductive element 140 includes an outer dielectric layer that substantially surrounds an interior-conducting layer, similar to the self-limiting electrosurgical electrodes described previously.

Referring again to FIG. 5, disposed on opposing sides of conductive element 140 are pads 142, 144. As can be seen, pad 142 has an outer surface 146 and an inner surface 148. Outer surface 146 is configured to be placed against the surface of a patient (thereby acting as a working surface of return electrode 132), while inner surface 148 is disposed next to conductive element 140. In some embodiments, inner surface 148 is secured to conductive element 140, such as with an adhesive, to prevent air bubbles or separation between pad 142 and conductive element 140. Pad 142 may include outer and inner cover layers that are formed individually and secured together about their edges or are integrally formed. The outer and inner cover layers may define outer and inner surfaces 146, 148. Outer and inner cover layers may be formed of various materials, such as urethane, polyurethane, polyethylene, polypropylene, polyolefins, polyvinyl chloride, PET, etc. A fill material 152, discussed below, may be disposed between the outer and inner cover layers.

Similar to pad 142, pad 144 includes an outer surface 154 and an inner surface 156. Outer surface 154 is configured to be placed on a support surface (e.g., operating table, chair, etc.), while inner surface 156 is disposed next to conductive element 140. Like outer and inner cover layers 146, 148, one or both of outer surface 154 and inner surface 156 may be defined by a cover layer formed of various materials, such as urethane, polyurethane, polyethylene, polypropylene, polyolefins, polyvinyl chloride, PET, etc. Like pad 142, inner surface 156 may be secured to conductive element 140, such as with an adhesive, to prevent air bubbles or separation between pad 144 and conductive element 140. In other embodiments, however, the edges of pad 144 may be secured to the edges of pad 142 with conductive element 140 disposed therebetween. Also like pad 142, pad 144 may include a fill material.

Fill materials used in pads 142, 144 may provide return electrode 132 with some pressure reducing characteristics. More specifically, since pads 142, 144 retain a defined volume of fill material, when an individual rests upon return electrode 132, the fill materials distribute the downward force of the patient throughout the fill materials, thereby decreasing the point forces applied to those parts of the patient's anatomy where bony prominences are located. Nevertheless, as discussed elsewhere herein, pads 142, 144 are relatively thin to ensure sufficient coupling between a patient and conductive element 140. Accordingly, in some situations, such as during lengthy surgical procedures, it may be desirable or necessary to use a separate pressure reducing pad in combination with return electrode 132 to prevent the formation of pressure sores on the patient or to increase the patient's comfort level.

Fill materials used in pads 142, 144 may act as dielectric layers to reduce the current that flows through pads 142, 144, respectively. Alternatively, the fill materials may take the form of conducting materials to aid with the transmission of current therethrough. Additionally, the fill materials may provide a thermal mass for the distribution of heat during an electrosurgical procedure. As discussed above, IEC requires that during an electrosurgical procedure the temperature rise of the patient's tissue should remain below six degrees Celsius (6° C.). The thermal mass provided by the fill materials assists with the distribution of heat throughout the patient's body and substantially eliminates, in combination with the self-limiting characteristics of return electrode 132, the potential for hot spots that may burn the patient. Consequently, the substances used for fill materials may perform multiple functions during an electrosurgical procedure.

In general, the fill materials may take the form of one or more solids, liquids, gases, or combinations thereof depending on the pressure reducing, dielectric, and/or conducting properties needed for return electrode 132. For example, in one illustrative embodiment, the fill materials are elastomeric gels having low durometer level, such as SORBOTHANE. In addition to SORBOTHANE, various other elastomeric gels may be used, such as but not limited to those based upon the polymer chemistry of urethanes, silicones, hydrophilic elastomers or hydrogels, vinyls, vinyl alcohols, or other similar materials and technologies. Additionally, the fill materials may take the form of water, saline, water based materials, conductive oils, and the like. Still further, the fill materials may take the form of solid but flexible foam-type materials.

The materials forming return electrode 132, conductive element 140, and pads 142, 144, at least partially control the passage of current from a patient to conductive element 140. As such, in one embodiment, pads 142, 144 are insulative. In an alternate configuration, pads 142, 144 may be conductive and aid in the passage of current from the patient to conductive element 140. So long as the return electrode 132 provides the self-limiting characteristics described herein, the various elements of return electrode 132, i.e., conductive element 140 and pads 142, 144, may provide one or more resistive, inductive, and/or capacitive inductance components to the bulk impedance of the return electrode. In this manner return electrode 132 is self-limiting, while also providing at least some pressure reducing characteristics.

In addition to the materials used to form pads 142, 144, the thickness and arrangement of pads 142, 144 and conductive element 140 can affect the transmission of current from a patient to conductive element 140. By way of non-limiting example, the distance between outer surface 146 of pad 142 and conductive element 140 can affect the capacitive coupling between conductive element 140 and a patient resting upon return electrode 132. Through this capacitive coupling, current used during electrosurgery is passed from the patient to return electrode 132. As will be understood by one of ordinary skill in the art in light of the disclosure herein, the capacitive coupling between the patient and return electrode 132 can be directly related to the self-limiting characteristics of return electrode 132. Thus, by changing the distance between the outer surface 146 and the conductive element 140, the capacitive coupling between the patient and the return electrode 132 can be adjusted.

As illustrated in FIG. 5, to make return electrode 132 safe and self-limiting for patients of substantially any size, the distance between surface 146 and conductive element 140 varies. More specifically, portions of conductive element 140 are disposed closer to outer surface 146 than other portions of conductive element 140. In the illustrated embodiment, for instance, conductive element 140 is arranged in an arch, domed, or other curved shape such that the portion of conductive element 140 within area 139 is positioned closer to outer surface 146 than the rest of conductive element 140. In some embodiments, for instance, at least a portion of conductive element 140 within area 139 is spaced apart from outer surface 146 by a distance of less than about 0.120 inches, about 0.11 inches, about 0.1 inches, about 0.09 inches, about 0.075 inches, about 0.06 inches, about 0.05 inches, about 0.03 inches, or about 0.02 inches. In other embodiments, at least a portion of conductive element 140 within area 139 is spaced apart from outer surface 146 by a distance of between about 0.02 inches and about 0.120 inches, between about 0.02 inches and about 0.11 inches, between about 0.02 inches and about 0.1 inches, between about 0.02 inches and about 0.09 inches, between about 0.02 inches and about 0.075 inches, between about 0.02 inches and about 0.06 inches, between about 0.02 inches and about 0.05 inches, between about 0.02 inches and about 0.03 inches, or within any ranges within the outer limits of the foregoing ranges. The spacing between conductive element 140 and outer surface 146 can be achieved by limiting the thickness of at least a portion of pad 142 within area 139 to the noted dimensions (e.g., less than about 0.120 inches, between about 0.02 inches and about 0.120 inches).

Positioning conductive element 140 closer to outer surface 146 increases the capacitive coupling with a patient (or portion of a patient) positioned on area 139. A smaller patient that has less surface area to contact return electrode 132 needs greater capacitive coupling with conductive element 140 in order to effectively and safely (e.g., in a self-limiting manner) transfer electrosurgical current to return electrode 132. Accordingly, a small patient can be placed on area 139 and the relatively small distance between outer surface 146 and conductive element 140 enables sufficient capacitive coupling between the patient and conductive element 140 to effectively and safely transfer electrosurgical current therebetween. In contrast, a larger patient that can make contact with a larger portion of return electrode 132 does not require the same high level of capacitive coupling with conductive element 140 as a small patient. Accordingly, the portion of conductive element 140 outside of area 139 can be spaced further from outer surface 146 while still providing sufficient capacitive coupling between the patient and conductive element 140. It will be appreciated that larger patients may also be positioned on area 139 alone or in addition to other portions of return electrode 132 and return electrode 132 will enable the effective and safe transfer of electrosurgical current.

In addition or as an alternative to adjusting the distance between the outer surface 146 and the conductive element 140, the dielectric constants of the materials used in pad 142 may be adjusted to achieve the desired level of capacitive coupling and/or resistance presented by return electrode 132. As is understood, the capacitance between the patient and the conductive element 140 is dependent on the thickness of pad 142 therebetween, the amount of contact area between the patient and return electrode 132, as well as the dielectric constants of the pad materials. Accordingly, the materials used to form pad 142 may be selected, as least in part, based upon the value of their dielectric constants. Similarly, the materials used in pad 142 may be altered (e.g., by levels of doping) to adjust their dielectric constants in order to provide the desired capacitance and/or resistance.

Thus, for instance, rather than or in addition to positioning the conductive element 140 closer to outer surface 146 in area 139 than outside of area 139, pad 142 may include areas that have different dielectric constants. By way of example, the portion of pad 142 that is within area 139 may have a dielectric constant that is different than the portion of pad 142 that is outside of area 139. In some embodiments, the portion of pad 142 within area 139 is formed of a different material than the portion of pad 142 outside of area 139, thereby providing the different dielectric constants for the different areas of pad 142. In other embodiments, pad 142 is made of the same material inside and outside of area 139, but the material within one of the portions is altered (e.g., by doping) to adjust the dielectric constant. As a result, the different areas of pad 142 have different dielectric constants.

As discussed elsewhere herein, previous self-limiting return electrodes were made for specific categories of patients. The categories were typically defined by patient weight ranges (e.g., less than 5 kg, 5 kg to 15 kg, and over 15 kg). In addition to selecting the proper return electrode based on the patient's weight, operating room personnel also needed to ensure that power settings on the electrosurgical generator were set in accordance with the restrictions associated with the particular return electrode used (e.g., to limit current to: 350 mA for patients under 5 kg; 500 mA for patients between 5 kg and 15 kg; and 700 mA for patients over 15 kg). Selecting the correct return electrode and making sure that the settings of the electrosurgical generator were properly set could be confusing and viewed as trivial matters for operating room personnel, especially those not familiar with the principles of electricity.

In contrast, return electrode 132 functions with patients of substantially any size. For instance, in one implementation, return electrode 132 may be used with patients that weigh 0.8 lb or more. In another implementation, return electrode 132 may be used with patients from multiple industry standard weight categories. For instance, return electrode 132 may be used on any patient regardless of whether that patient falls within IEC's less than 5 kg category, 5 kg to 15 kg category, or above 15 kg category. Furthermore, since return electrode 132 can be used with substantially any sized patient, operating personnel do not have to limit or adjust the generator power settings to accommodate different return electrodes.

Figure 6:
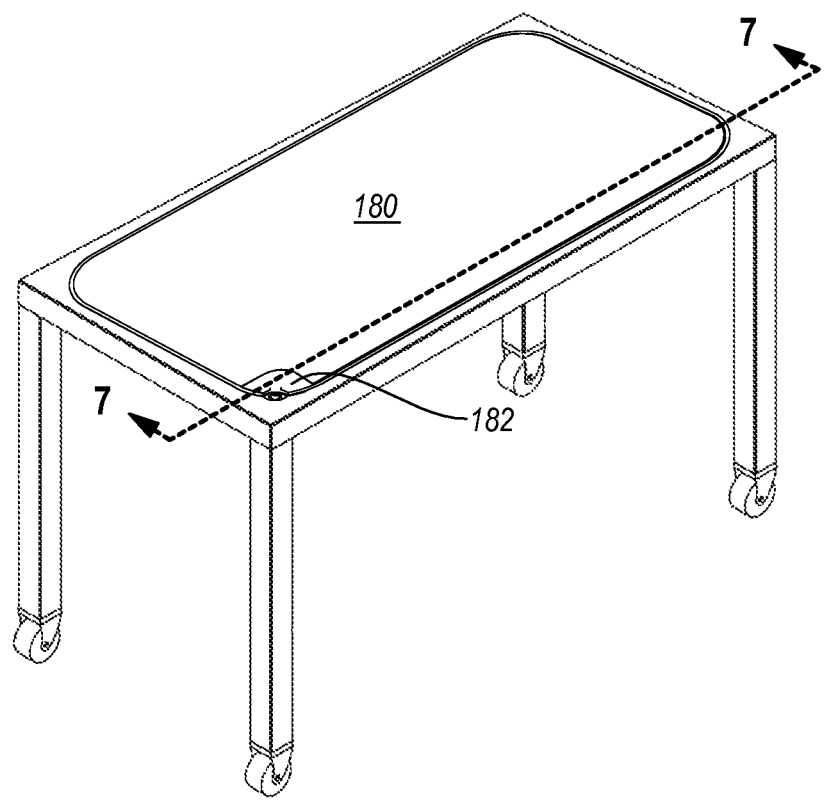
FIG. 6 is a perspective view showing an operating table with an electrosurgical return electrode according to the present disclosure disposed on the upper surface thereof.

Attention is now directed to FIGS. 6-8, which illustrate an electrosurgical return electrode 180 according to the present disclosure. FIG. 6 illustrates return electrode 180 on operating table 130. Similar to return electrode 132, return electrode 180 includes an electrical connector 182 to provide a conventional electrical return to the electrosurgical radio frequency energy source.

FIG. 7 illustrates a simplified section taken along the lines 7-7 of FIG. 6 and FIG. 8 illustrates an exploded view of return electrode 180. As illustrated in FIGS. 7 and 8, return electrode 180 includes a conductive element 184 and pads 186, 188 on opposing sides of conductive element 184. Conductive element 184, in one configuration, may be similar to conductive element 140. Nevertheless, it may be appreciated by one skilled in the art that conductive element 184 may have various other configurations so long as conductive element 184 is capable of performing the functions of an electrode, i.e., being capable of passing current therethrough.

Referring again to FIGS. 7 and 8, disposed on opposing sides of conductive element 184 are pads 186, 188. As can be seen, pad 186 has an outer cover layer 190 and an inner cover layer 192 that define an interior chamber 194 therebetween. Outer cover layer 190 is configured to be placed against the surface of a patient (thereby acting as a working surface of return electrode 180), while inner cover layer 192 is disposed next to conductive element 184. In some embodiments, inner cover layer 192 is secured to conductive element 184, such as with an adhesive, to prevent air bubbles or separation between pad 186 and conductive element 184. Outer and inner cover layers 190, 192 may be formed individually and secured together about their edges or may be integrally formed. Outer and inner cover layers 190, 192 may be formed of various materials, such as urethane, polyurethane, polyethylene, polypropylene, polyolefins, polyvinyl chloride, PET, etc. A fill material 196, similar to that discussed elsewhere herein, may be disposed in interior chamber 194.

Similar to pad 186, pad 188 includes an outer cover layer 198 and a fill material 200. Outer cover layer 198 is configured to be placed against the surface of a patient (thereby acting as a second working surface of return electrode 180), while fill material 200 is disposed next to conductive element 184. Like outer and inner cover layers 190, 192, outer cover layer 198 may be formed of various materials, such as urethane, polyurethane, polyethylene, polypropylene, polyolefins, polyvinyl chloride, PET, etc.

Rather than having a second inner cover layer, pad 188 may be formed during the assembly of return electrode 180. For instance, during assembly of return electrode 180, chamber 194 in pad 186 may be filled with material 196 and sealed closed such that material 196 cannot escape from chamber 194. Pad 186 may be disposed next to and/or secured to a first major surface of conductive element 184. The edges of outer cover layer 198 may then be secured to the edges of pad 186 so as to create a chamber between conductive element 184 and outer cover layer 198. The newly defined chamber may then be filled with material 200 and sealed closed to retain material 200 therein.

It will be appreciated that pads 186, 188 may be similar or identical to one another. For instance, in addition to outer cover layer 198 and material 200, pad 188 may also include an inner cover layer (similar to inner cover layer 192) that cooperates with outer cover layer 198 to define a chamber for receiving material 200. Furthermore, pad 188 may also be secured to conductive element 184. For instance, in embodiments where pad 188 includes an inner cover layer, the inner cover layer may be secured, such as with an adhesive, to a second major surface of conductive element 184. Likewise, pad 186 may be similar to pad 188 in that pad 186 may be formed without inner cover layer 192.

The materials forming return electrode 180, conductive element 184, and pads 186, 188, control the passage of current from a patient to conductive element 184. As such, in one embodiment, pads 186, 188 and fill materials 196, 200 are insulative, while, in an alternate configuration, pads 186, 188 and/or materials 196, 200 may be conductive and aid in the passage of current from the patient to conductive element 184. So long as return electrode 180 provides the self-limiting characteristics described herein, the various elements of return electrode 180, i.e., conductive element 184 and pads 186, 188, may provide one or more resistive, inductive, and/or capacitive inductance components to the bulk impedance.

In addition to the materials used to form pads 186, 188, the thickness of pads 186, 188 can affect the transmission of current from a patient to conductive element 184. By way of non-limiting example, forming pads 186, 188 relatively thin can facilitate capacitive coupling between conductive element 184 and a patient resting upon return electrode 180. Through this capacitive coupling, current used during electrosurgery is passed from the patient to return electrode 180. As will be understood by one of ordinary skill in the art in light of the disclosure herein, the capacitive coupling between the patient and return electrode 180 can be directly related to the self-limiting characteristics of return electrode 180. Thus, making pads 186, 188 relatively thin contributes to good electrical coupling between the patient and return electrode 180 so as to enable safe and effective electrosurgery for substantially any sized patient. Accordingly, one or both of pads 186, 188 may have a thickness within a predetermined range. For instance, in some embodiments, one or both of pads 186, 188 has an approximate thickness of between about 0.02 inches and about 0.120 inches. In other embodiments, one or both of pads 186, 188 has an approximate thickness of less than about 0.10 inches, about 0.09 inches, about 0.075 inches, about 0.06 inches, about 0.05 inches, about 0.03 inches, or about 0.02 inches. In some embodiments, return electrode 180 has a total thickness of about 0.135 inches or less.

The inclusion of pads 186, 188, which are substantially similar to one another, on opposing sides of conductive element 184 provides return electrode 180 with a substantially symmetrical construction. The symmetrical nature of return electrode 180 provides return electrode 180 with two surfaces that function as working surfaces. More specifically, the major surfaces of return electrode 180 defined by outer cover layers 192, 198 may each be used as a working surface. For instance, return electrode may be positioned so that outer cover layer 192 is positioned towards a patient and return electrode 180 will exhibit the self-limiting characteristics discussed herein. Likewise, return electrode 180 can be turned over so that outer cover layer 198 is positioned against a patient and return electrode 180 will exhibit the self-limiting characteristics discussed herein.

As discussed elsewhere herein, previous return electrodes were made for specific categories of patients. The categories were typically defined by patient weight ranges (e.g., less than 5 kg, 5 kg to 15 kg, and over 15 kg). In addition to selecting the proper return electrode based on the patient's weight, operating room personnel also needed to ensure that power settings on the electrosurgical generator were set in accordance with the restrictions associated with the particular return electrode used (e.g., to limit current to: 350 mA for patients under 5 kg; 500 mA for patients between 5 kg and 15 kg; and 700 mA for patients over 15 kg). Selecting the correct return electrode and making sure that the settings of the electrosurgical generator were properly set could be confusing and viewed as trivial matters for operating room personnel, especially those not familiar with the principles of electricity.

In contrast, return electrode 180 functions with patients of substantially any size. For instance, in one implementation, return electrode 180 may be used with patients that weigh 0.8 lb or more. In another implementation, return electrode 180 may be used with patients from multiple industry standard weight categories. For instance, return electrode 180 may be used on any patient regardless of whether that patient falls within IEC's less than 5 kg category, 5 kg to 15 kg category, or above 15 kg category. Furthermore, since return electrode 180 can be used with substantially any sized patient, operating personnel do not have to limit or adjust the generator power settings to accommodate different return electrodes.

Figure 9:
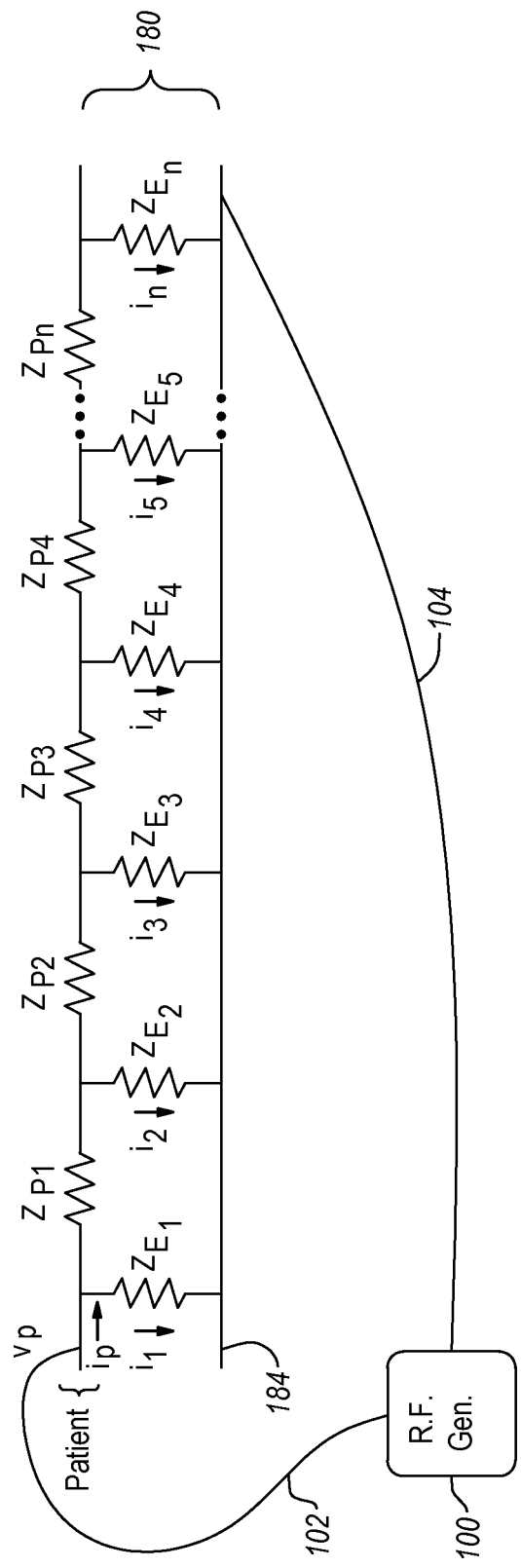
FIG. 9 is a simplified electrical schematic diagram illustrating typical resistances encountered by radio frequency current during an operative procedure with the electrode of FIG. 6.

As noted elsewhere herein, prior self-limiting return electrodes were designed based on the assumption that patients are purely conductive and, therefore sought to uniformly distribute the electrosurgical current over the entire contact area between the patient and the electrode. In contrast, the return electrodes of the present disclosure are designed with the understanding that patients are both conductive and resistive. FIG. 9 illustrates a simplified electrical schematic diagram of a patient lying on return electrode 180, and electrical conductors 102 and 104 electrically connecting the patient and return electrode 180 to generator 100.

Generally, the patient and conductive element 184 of return electrode 180 may be thought of as opposing plates of a parallel capacitor. Unlike the plates from traditional parallel plate capacitors, however, the patient is not purely conductive. Rather, as illustrated in FIG. 9, the patient is both conductive and resistive. In particular, portions of the patient are conductive while other portions of the patient (represented by $Z_{P1}$-$Z_{Pn}$) are resistive. Thus, when electrosurgical current is transmitted from generator 100 to the patient via conductor 102, the resistive portions of the patient will resist spread of the electrosurgical current through the patient.

To accommodate for the fact that the patient's own resistance will resist the even spread of the electrosurgical current throughout the patient, return electrode 180 is designed to allow for the non-uniform transfer of the electrosurgical current from the patient to conductive element 184. More specifically, return electrode 180 is designed to allow for more current to be transmitted from the patient to conductive element 184 near the surgical site than away from the surgical site while still providing the self-limiting characteristics discussed herein.

Return electrode 180 has resistive properties that resist the transfer of current from the patient to conductive element 184. As illustrated in FIG. 9, the resistance presented by return electrode 180 may be conceptually thought of as individual resistors $Z_{E1}$-$Z_{En}$, each of which is associated with an area of return electrode 180. Nevertheless, it will be understood that return electrode 180 may not necessarily be formed of individual resistors, but electrically return electrode 180 may function as though it were.

During an electrosurgical procedure, conductor 102 may transmit electrosurgical current to the patient in the area of the patient illustrated in FIG. 9. As the current begins to spread through the patient, the current will encounter the resistance $Z_{P1}$ presented by some of the patient's tissue. Because of the resistance provided by $Z_{P1}$, the current will seek an alternate path, which is presented by $Z_{E1}$ of return electrode 180. The values of $Z_{P1}$ and $Z_{E1}$ will determine how much of the current will spread to other portions of the patient (e.g., through $Z_{P1}$) and how much of the current will be transmitted to conductive element 184. At least some of the current will pass through $Z_{P1}$ and encounter $Z_{P2}$ presented by patient tissue and $Z_{E2}$ presented by return electrode 180. Again, the values of each will determine how much current passes through each of $Z_{P2}$ and $Z_{E2}$. This process will continue until all of the current is transferred to the conductive element 184 and/or throughout the portion of the patient that is in contact with return electrode 180.

The effective impedance $Z_{eff}$ for this type of patient/electrode system can be estimated or approximated by an infinite impedance ladder, which is defined by:

$$Z_{eff} = Z_P + Z_E \| Z_{eff} \quad (2)$$

Equation 2 can be expanded to:

$$Z_{eff} = Z_P + \frac{Z_E \times Z_{eff}}{Z_E + Z_{eff}} \quad (3)$$

Solving Equation 3 for $Z_{eff}$ provides:

$$Z_{eff} = \frac{Z_P}{2} + \sqrt{\frac{(Z_P)^2}{4} + Z_P \times Z_E} \quad (4)$$

Furthermore, it is well known that current is directly proportional to voltage and inversely proportional to resistance (or impedance). Accordingly, when a voltage $V_P$ is applied between the patient and the return electrode 180, the incoming current $i_P$ is defined as:

$$i_P = \frac{V_P}{Z_{eff}} \quad (5)$$

Substituting Equation 4 into Equation 5 and simplifying provides:

$$i_P = \frac{V_P}{2Z_P} \quad (6)$$

Assuming that the ratio between the return electrode impedance $Z_E$ and the patient resistance $Z_P$ is 2, it can be shown that currents $i_1, i_2, i_3, \ldots, i_n$ are defined as follows:

$$i_1 = \frac{V_P - Z_P i_P}{2Z_P} = \frac{i_P}{2} \quad (7)$$

$$i_2 = \frac{i_1 2Z_P - (i_P - i_1)Z_P}{2Z_P} = \frac{i_1}{2} \quad (8)$$

$$i_3 = \frac{i_2 2Z_P - (i_1 - i_2)Z_P}{2Z_P} = \frac{i_2}{2} \quad (9)$$

$$i_n = \frac{i_{n-1} 2Z_P - (i_{n-2} - i_{n-1})Z_P}{2Z_P} = \frac{i_{n-1}}{2} \quad (10)$$

Thus, it can be seen that the current through each branch or segment of the return electrode may be half the current through the previous branch. In such an embodiment, over 90% of the total current entering the patient would be contained in the first four branches of the return electrode. If the return electrode was made up of 100 branches, 90% of the total current would be focused into 4% of the total surface area of the pad. Similarly, if the ratio between the return electrode impedance $Z_E$ and the patient resistance $Z_P$ were 20, the same calculation method shows that 59% of the total current entering the patient would be contained within the first four branches of the return electrode.

The foregoing example $Z_E/Z_P$ ratios demonstrate that the current density across the effective surface area between a patient and a return electrode can be adjusted. Additionally, these examples illustrate that the size of the effective surface area can be adjusted. Thus, while the impedance presented by the patient cannot be adjusted, the impedance of the return electrodes of the present disclosure can be tailored to provide the described self-limiting properties as well as safe functionality with patients of substantially any size due at least in part to the non-uniform current distribution described herein.

Materials and geometries may be selected for return electrode 180 so that the resistance presented by return electrode will allow more current to be transmitted from the patient to conductive element 184 near the surgical site as opposed to requiring an even distribution of the current being transmitted therebetween. By way of example, limiting the thickness of pads 186, 188 to below about 0.120 inches, about 0.10 inches, about 0.09 inches, about 0.075 inches, about 0.06 inches, about 0.05 inches, about 0.03 inches, or about 0.02 inches can enable return electrode 180 to present a level of resistance that allows for uneven distribution of current being transferred from a patient to conductive element 184. For instance, as described above, return electrode 180 can be configured to allow more current to be transferred through $Z_{RE1}$ than through $Z_{E2}$, and more current through $Z_{E2}$ than through $Z_{E3}$, and so on. Furthermore, restraining the thickness of pads 186, 188 can also facilitate improved capacitive coupling between conductive element 184 and patients of substantially any size, thereby allowing return electrode 180 to be safely used with patients of substantially any size.

In addition or as an alternative to adjusting the thickness of pads 186, 188 (e.g., limiting the thickness to the dimensions identified herein), the dielectric constants of the materials used in pads 186, 188 may be adjusted to achieve the desired level of capacitive coupling and/or resistance presented by return electrode 180. As noted above, the capacitance between the patient and the conductive element 184 is dependent on the thickness of the pad (e.g., pads 186, 188) therebetween, the amount of contact area between the patient and return electrode 180, as well as the dielectric constants of the pad materials. Accordingly, the materials used to form pads 186, 188 may be selected, at least in part, based upon the value of their dielectric constants. Similarly, the materials used in pads 186, 188 may be altered (e.g., by doping) to adjust their dielectric constants in order to provide the desired capacitance and/or resistance.

Attention is now directed to FIGS. 10-14, which illustrate additional example embodiments of return electrodes that allow for the non-uniform distribution of current densities over the effective contact area between a patient and the return electrode, which, as discussed herein, allows for the return electrodes to be safely and effectively used with patients of substantially any size. It will be appreciated that the return electrodes of FIGS. 10-14 may be similar or identical to the above-described return electrodes in many aspects. Accordingly, the following description of the return electrodes of FIG. 10-14 will focus primarily on the features that are different than those previously described.

Figure 10:
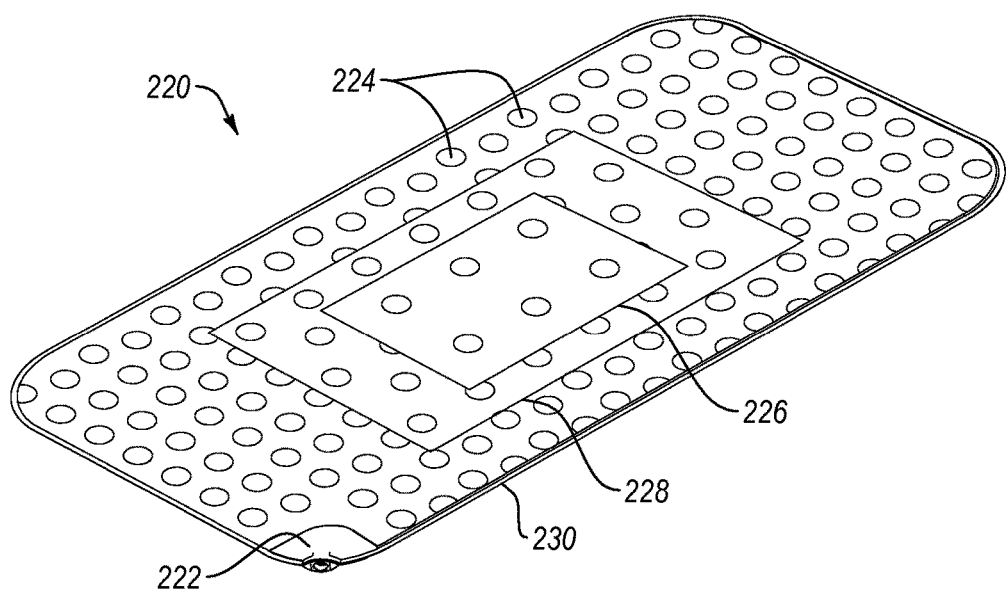
FIG. 10 is a perspective view showing an electrosurgical return electrode according to the present disclosure.

FIG. 10 illustrates a perspective view of a return electrode 220. As noted, return electrode 220 may be similar or identical to the other embodiments described herein in some aspects. For instance, return electrode 220 includes a conductive element, a connector 222, and a pad disposed on each side of the conductive element. Like return electrode 180, return electrode 220 may be reversible. That is, return electrode 220 may have two opposing major surface that can be alternately used as working surfaces during electrosurgical procedures.

The conductive element defines a plurality of apertures or openings 224 extending therethrough. In the illustrated embodiment, the plurality of apertures 224 are arranged in three distribution areas. The first distribution area 226 is positioned near the center of return electrode 220. As can be seen, there are relatively few apertures within first distribution area 226 and they are spread apart from one another. The second distribution area 228 is disposed concentrically about first distribution area 226. Second distribution area 228 includes a higher density of apertures 224 than first distribution area 226. The third distribution area 230 is disposed concentrically about second distribution area 228 and includes a higher density of apertures 224 than first and second distribution areas 226, 228.

Although apertures 224 are illustrated as being circular in shape, it will be understood that the apertures could have substantially any shape, including rectangular, square, oval, triangular, and the like. Additionally, while apertures 224 are illustrated as having generally uniform distributions within each of the distribution areas, the apertures could also have non-uniform distributions within one or more of the distribution areas. Furthermore, although distribution areas 226, 228, 230 are illustrated as being generally rectangular in shape, the distribution areas may have substantially any shape. For instance, the distribution areas may be circular, oval, rectangular, and the like. Moreover, while distribution areas 226, 228, 230 are illustrated as being general discreet areas (e.g., each area has a particular aperture density), the distribution areas may be less discreet and more continuously changing (e.g., the aperture distribution density continuously decreases away from the center of the return electrode). For instance, the distribution density of the apertures may gradually change within one or more of the distribution areas and/or across multiple distribution areas. By way of example, apertures may be formed in concentric rings, with each ring having an aperture density that is less dense than an aperture density of an adjacent internal ring.

Similar to tailoring the dielectric value or the thickness of the pads as discussed above, including apertures 224 in the conductive element affects the capacitive coupling between the patient and the conductive element. Areas with fewer or less densely arranged apertures in the conductive element will allow for better capacitive coupling than areas with more or more densely arranged apertures. As a result, the different aperture distribution areas provide for the non-uniform current density features discussed herein. Thus, for example, area 226 may provide sufficient capacitive coupling for a small patient (e.g., under 5 kg), while areas 228, 230 provide sufficient capacitive coupling for medium (e.g., between 5 kg to 15 kg) and large (e.g., above 15 kg) patients, respectively.

It will be appreciated that a return electrode similar to return electrode 220 may include fewer or more than three aperture distribution areas. Additionally, the different aperture distribution areas may be otherwise arranged relative to one another. For instance, aperture distribution area 226 may be arranged near an end and along at least a portion of the width of the return electrode. In other embodiments, two aperture distribution areas 226 may be included, one near a first end of the return electrode and the second near a second end of the return electrode.

The various aperture distribution areas may be visually identifiable via one or more visual indicators. For instances, each area may be color coded, labeled, or have area identifying indicia. The one or more visual indicators may identify the best position on the return electrode for a particular patient, such as based on the patient's weight.

Figure 11:
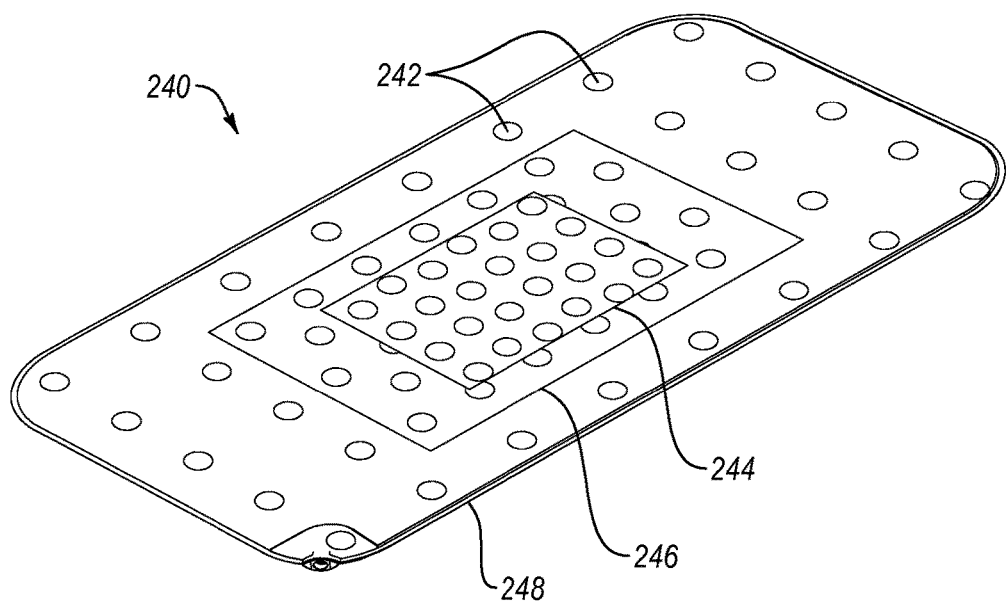
FIG. 11 is a perspective view showing another electrosurgical return electrode according to the present disclosure.

FIG. 11 illustrates a return electrode 240 that is similar to return electrode 220. Instead of having apertures extending through the conductive element, however, the conductive element of return electrode 240 includes a plurality of protrusions 242 that extend toward the outer surface(s) of the return electrode. In the illustrated embodiments, the protrusions 242 are arranged in three protrusion distribution areas 244, 246, 248. Like return electrodes 180, 220, return electrode 240 may be reversible. That is, return electrode 240 may have two opposing major surface that can be alternately used as working surfaces during electro surgical procedures.

Protrusions 242 may take a variety of forms. For instance, protrusions 242 may take the form of generally semi-spherical bumps that extend away from one or more major surfaces of the conductive element. Protrusions 242 may be integrally formed with the rest of the conductive element, or protrusions 242 may be secured to the major surface(s) of the conductive element.

Due to the increased height of the protrusions 242 (compared to the major surface(s) of the conductive element), better capacitive coupling can be achieved between a patient and the protrusions 242 than between the patient and the rest of the conductive element. Accordingly, areas of return electrode 240 that include more or more densely arranged protrusions 242 will allow for better capacitive coupling than areas with fewer or less densely arranged protrusions 242. As a result, the different protrusion distribution areas provide for the non-uniform current density features discussed herein. Thus, for example, area 244 may provide sufficient capacitive coupling for a small patient (e.g., under 5 kg), while areas 246, 248 provide sufficient capacitive coupling for medium (e.g., between 5 kg to 15 kg) and large (e.g., above 15 kg) patients, respectively.

It will be appreciated that a return electrode similar to return electrode 240 may include fewer or more than three protrusion distribution areas. Additionally, the different protrusion distribution areas may be otherwise arranged relative to one another. Additionally, the protrusion distribution areas may have other shapes and the protrusion distribution densities may be discreet or more continuously changing (e.g., the protrusion distribution density continuously increases away from the center of the return electrode). Moreover, the various protrusion distribution areas may be visually identifiable via one or more visual indicators (e.g., color coding, labels, identifying indicia, etc.).

FIG. 12 illustrates a cross-section of yet another embodiment of a return electrode 250 according to the present disclosure. Similar to the other return electrodes described herein, return electrode 250 includes a conductive element 252 and pads 254, 256 disposed on opposing sides thereof. Similar to conductive element 140 (FIG. 5), conductive element 252 has a non-planar configuration. More specifically, as shown in FIG. 12, conductive element 252 has a wavy configuration, similar to a sinusoidal wave with alternating peaks and valleys. As can be seen in FIG. 12, the peaks and valleys are positioned relatively close to the external surfaces of return electrode 250. In some embodiments, the alternating peaks and valleys enable return electrode 250 in a reversible manner (e.g., opposing major surfaces of return electrode 250 can be used as working surfaces during electrosurgical procedures).

As can also be seen in FIG. 12, conductive element 250 has multiple distribution areas 258, 260, 262. In distribution area 258, the peaks and valleys formed by conductive element 252 are positioned close together. In distribution area 260, the peaks and valleys are more spread apart than in distribution area 258, and in distribution area 262 the peaks and valleys are even further spread apart. The relative spacing of the peaks and valleys in the different distribution areas allows for different levels of capacitive coupling between the patient and return electrode 250. For instance, the relatively close spacing of the peaks and valleys in distribution area 258 allows for better capacitive coupling to be achieved between a patient and the conductive element than between the patient and the more spread out portions of the conductive element in distribution areas 260, 262. As a result, the different distribution areas provide for the non-uniform current density features discussed herein. Thus, for example, area 258 may provide sufficient capacitive coupling for a small patient (e.g., under 5 kg), while areas 260, 262 provide sufficient capacitive coupling for medium (e.g., between 5 kg to 15 kg) and large (e.g., above 15 kg) patients, respectively.

It will be appreciated that a return electrode similar to return electrode 250 may include any number of distribution areas. Additionally, the different distribution areas may be otherwise arranged relative to one another and the distribution densities of the peaks and valleys may be discreet or more continuously changing (e.g., the peaks and valley distribution density continuously decreases away from the center of the return electrode). Additionally, the various distribution areas may be visually identifiable via one or more visual indicators (e.g., color coding, labels, identifying indicia, etc.).

FIG. 13 illustrates a cross-section of a return electrode 270 that includes multiple conductive elements 272, 274, 276 and multiple pads 278, 280, 282, 284. As can be seen, pads 278, 284 form the opposing surfaces 286, 288 of return electrode 270. First conductive element 272 is positioned a first distance from surface 286. Second conductive element 274 is separated from first conductive element 272 by pad 280 and is positioned a second distance from surface 286. Similarly, third conductive element 276 is separated from second conductive element 274 by pad 282 and is positioned a third distance from surface 286.

The distance between each of conductive elements 272, 274, 276 and surface 286 and/or the dielectric constants of the layers positioned therebetween can be selected to provide desired levels of capacitive coupling for patients of different weights as described elsewhere herein. For instance, the distance between first conductive element 272 and surface 286 and/or the dielectric constant of pad 278 can provide a desired level of capacitive coupling for a patient under 5 kg. Similarly, the distance between second conductive element 274 and surface 286 and/or the dielectric constants of pads 278, 280 can provide a desired level of capacitive coupling for a patient between 5 kg and 15 kg. Likewise, the distance between third conductive element 276 and surface 286 and/or the dielectric constants of pads 278, 280, 282 can provide a desired level of capacitive coupling for a patient over 15 kg.

Each of conductive elements 272, 274, 276 can be connected to a dedicated electrical connector (similar to connectors 138, 182). Thus, for example, if a patient under 5 kg were to be operated upon, the patient could be positioned on surface 286 and return electrode 170 could be connected to an ESU via the connector associated with conductive element 272. Alternatively, each of conductive elements 272, 274, 276 can be connected to a single connector that allows for the selection of the desire conductive element. For instance, the connector may include a switching component that selectively makes electrical connection to a desired conductive element. Alternatively, the connector may be configured to receive different cable connectors. Reception of the different cable connectors in the connector may make electrical connection to a different one of the conductive elements.

FIG. 14 illustrates a cross-section of a return electrode 290 that includes multiple conductive elements 292, 294 and multiple pads 296, 298, 300. As can be seen, pads 296, 300 form the opposing surfaces 302, 304 of return electrode 290. First conductive element 292 is positioned a first distance from surface 302. Second conductive element 2294 is separated from first conductive element 292 by pad 298 and is positioned a second distance from surface 304. As with the other pads described herein, pads 296, 298, 300 can be formed of various materials, including gel, fluid, foam, gas, water, and the like, so as to impart various characteristics to return electrode 290 (e.g., cushioning, pressure reduction, heat distribution, conductivity levels, current density distribution, weight reduction, etc.).

The distance between conductive element 292 and surface 302 and/or the dielectric constant of pad 296 can be selected to provide desired levels of capacitive coupling for patients within a particular weight range. For instance, the distance between first conductive element 292 and surface 302 and/or the dielectric constant of pad 296 can provide a desired level of capacitive coupling for a patient under 10 kg. Similarly, the distance between second conductive element 294 and surface 304 and/or the dielectric constant of pad 300 can provide a desired level of capacitive coupling for a patient over 10 kg. Thus, for example, if a patient under 10 kg is to be operated upon, return electrode 290 can be positioned with surface 302 facing up. The patient can be placed upon surface 302 and the desired level of capacitive coupling will be provided between the patient and conductive element 292. In contrast, if a patient over 10 kg is to be operated upon, return electrode 290 can be positioned with surface 304 facing up. The patient can be positioned on surface 304 and the desired level of capacitive coupling will be provided between the patient and conductive element 294.

One or both of surfaces 302, 304 may include one or more visual indicators (e.g., color coding, labels, identifying indicia, etc.) that indicate what type of patient that particular surface should be used with. For instance, surface 302 may include one or more visual indicators identifying that surface 302 should be used with patients under 10 kg, while surface 304 may include one or more visual indicators identifying that surface 304 should be used with patients over 10 kg.

Implementations of the present disclosure may also take the form of methods for safely performing electrosurgical procedure, including by safely transferring electrosurgical current in non-uniform current densities from a patient to an electrosurgical return electrode via capacitive coupling. Such methods may include passively controlling an impedance of a return electrode. Passively controlling the impedance of a return electrode may be a result of particular structural features of the return electrode. Thus, passively controlling the impedance of a return electrode may be a result of the formation or construction of the return electrode, rather than active electrical adjustments (e.g., such as those made with contract quality monitoring systems) made during an electrosurgical procedure.

By way of example, passively controlling an impedance of a return electrode may include positioning a first conductive element of the return electrode at a first predetermined distance from a working surface of the return electrode. In some embodiments, this may be accomplished by limiting the thickness of a pad that forms the working surface and that separates the working surface from the conductive element.

As noted herein, some return electrode may include multiple conductive elements. Thus, passively controlling an impedance of a return electrode may include positioning a second conductive element of the return electrode at a second predetermined distance from the working surface of the return electrode, and, optionally, positioning a third conductive element of the return electrode at a third predetermined distance from the working surface of the return electrode. In embodiments that include multiple conductive elements, passively controlling the impedance of the return electrode may also include selecting one of the multiple conductive elements for conducting electrosurgical current from the patient.

In addition or as an alternative to controlling the distance between a conductive element and a working surface, passively controlling an impedance of the return electrode can include selecting one or more dielectric constants of a pad of the return electrode, the pad being disposed between a conductive element of the return electrode and the working surface of the return electrode.

Passively controlling an impedance of the return electrode may also include providing one or more structural surface features on a conductive element of the return electrode. In some embodiments, providing one or more structural surface features on a conductive element includes forming one or more apertures through the conductive element. Forming the one or more apertures through the conductive element may include forming two or more aperture distribution areas in the conductive element, where a first aperture distribution area has a first aperture distribution density and a second aperture distribution area has a second aperture distribution density that is different than the first aperture distribution density.

In other embodiments, providing one or more structural surface features on a conductive element includes forming one or more protrusions on the conductive element. Forming the one or more protrusions on the conductive element may include forming two or more protrusion distribution areas on the conductive element, where a first protrusion distribution area has a first protrusion distribution density and a second protrusion distribution area has a second protrusion distribution density that is different than the first protrusion distribution density.

In still other embodiments, passively controlling an impedance of the return electrode may include forming a conductive element of the return electrode in a non-planar configuration, such as in an arch, domed, or curved configuration. Forming the conductive element of the return electrode in a non-planar configuration may also include forming the conductive element in a wavy configuration such that the conductive element forms alternating peaks and valleys.

In further embodiments, passively controlling an impedance of the return electrode may include positioning a first conductive element of the return electrode at a first predetermined distance from a first working surface of the return electrode, positioning a second conductive element of the return electrode at a second predetermined distance from a second working surface of the return electrode, and selectively using either the first working surface or the second working surface based on a weight or size category of the patient being operated upon.

It will now be evident that there have been described herein improved universal electrosurgical return electrodes. The disclosed universal return electrodes are more versatile than prior return electrodes. For instance, the improved return electrodes are safely usable across multiple categories of patients. Thus, rather than needing different sized return electrodes for different sized patients, the improved return electrodes disclosed herein can be used with substantially any sized patient (e.g., 0.8 lbs. and above). Furthermore, because the disclosed return electrodes can be safely used with substantially any sized patient, operating room personnel do not have to adjust the settings of an electrosurgical generator according to the limitations of different return electrodes (e.g., different sized sticky pads). Additionally, some of the improved return electrodes disclosed herein provide multiple working surfaces. As a result, the return electrode can be placed with either major surface toward a patient and the return electrode will perform as desired. Making both major surfaces of the return electrode function as working surfaces eliminates the risk that a non-working surface will be placed against a patient during a surgical procedure.

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A reversible safety electrosurgical return electrode comprising:
   a conductive element configured to conduct electrical current, the conductive element having a first planar major surface and an opposing second planar major surface, the first planar major surface and the second planar major surface facing in opposite directions from one another;
   a first pad positioned adjacent the first planar major surface of the conductive element, wherein the first pad and the conductive element cooperate to define a first working surface of the reversible electrosurgical return electrode on a first side of the reversible electrosurgical return electrode; and
   a second pad positioned adjacent the second planar major surface of the conductive element such that the conductive element is disposed between and at least partially separates the first pad and the second pad from one another, wherein the second pad and the conductive element cooperate to define a second working surface of the reversible electrosurgical return electrode on a second side of the reversible electrosurgical return electrode opposite to the first side, the first working surface and the second working surface facing in opposite directions from one another,
   wherein the reversible electrosurgical return electrode is configured to have either the first working surface or the second working surface positioned toward a patient during an electrosurgical procedure such that either the first working surface or the second working surface is positioned between the patient and the conductive element and such that electrical current can be transferred between the patient and the conductive element through whichever of the first working surface or the second working surface is disposed between the patient and the conductive element.

2. A reversible safety electrosurgical return electrode according to claim 1, wherein the first pad comprises an inner cover layer and an outer cover layer that define an interior chamber.

3. A reversible safety electrosurgical return electrode according to claim 2, wherein the interior chamber is filled with a material selected from the group consisting of a visco-elastic material, a gel, water, saline, a water based material, a conductive oil, or combinations thereof.

4. A reversible safety electrosurgical return electrode according to claim 2, wherein the inner cover layer is secured to the first planar major surface of the conductive element.

5. A reversible safety electrosurgical return electrode according to claim 1, wherein the second pad comprises an outer cover layer and a fill material.

6. A reversible safety electrosurgical return electrode according to claim 5, wherein edges of the outer cover layer of the second pad are attached to edges of the first pad with the conductive element disposed between the first and second pads.

7. A reversible safety electrosurgical return electrode according to claim 5, wherein the outer cover layer of the second pad and the conductive element at least partially define a second interior chamber in which the fill material of the second pad is disposed.

8. A reversible safety electrosurgical return electrode according to claim 1, wherein the reversible safety electrosurgical return electrode is configured such that electrical current transferred from a patient to the conductive element is transmitted non-uniformly over the portion of the reversible safety electrosurgical return electrode that is contacted by the patient.

9. A reversible safety electrosurgical return electrode according to claim 1, wherein each of the first pad and the second pad has a thickness between about 0.02 inches and about 0.120 inches.

10. A reversible safety electrosurgical return electrode according to claim 1, wherein the reversible safety electrosurgical return electrode is configured to be safely used with patients from multiple industry standard weight categories.

11. A method for safely transferring electrosurgical current in non-uniform current densities from a patient to an electrosurgical return electrode via capacitive coupling, comprising:
    passively controlling an impedance of the return electrode, comprising:
      providing a plurality of apertures through a conductive element of the electrosurgical return electrode, the plurality of apertures being divided into a first area and a second area, the first area having a first aperture distribution density and the second area having a second aperture distribution density that is different than the first aperture distribution density, each of the first area and the second area having one or more visual indicators to identify and/or distinguish the first area and the second area from one another, wherein:
        the first aperture distribution density is configured to transfer electrical current between the conductive element and a patient at a first electrical current density such that the first area is configured for use with patients from a first predetermined category; and
        the second aperture distribution density is configured to transfer electrical current between the conductive element and a patient at a second electrical current density such that the second area is configured for use with patients from a second predetermined category; and
      positioning a patient on the first area or the second area depending on whether the patient is from the first predetermined category or the second predetermined category.

12. A method according to claim 11, wherein the first aperture distribution density has a lower density of apertures than the second aperture distribution density.

13. A method according to claim 11, wherein the first aperture distribution density has a higher density of apertures than the second aperture distribution density.

14. A method according to claim 11, wherein the plurality of apertures are divided into the first area, the second area, and a third area, the third area having a third aperture distribution density that is different than the first and second aperture distribution densities.

15. A method according to claim 14, wherein the third aperture distribution density is configured to transfer electrical current between the conductive element and a patient at a third electrical current density such that the third area is configured for use with patients from a third predetermined category.

\* \* \* \* \*